US008388962B2

(12) United States Patent
Karin et al.

(10) Patent No.: US 8,388,962 B2
(45) Date of Patent: Mar. 5, 2013

(54) MOLECULES AND METHODS OF USING SAME FOR TREATING MCP-1/CCR2 ASSOCIATED DISEASES

(75) Inventors: Nathan Karin, Haifa (IL); Gizi Wildbaum, Kiryat Yam (IL); Yaniv Zohar, Kiryat-Haim (IL); Liat Izhak, Kiryat-Yam (IL); Uri Weinberg, Haifa (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 1503 days.

(21) Appl. No.: 11/883,725

(22) PCT Filed: Apr. 10, 2006

(86) PCT No.: PCT/IL2006/000454
§ 371 (c)(1),
(2), (4) Date: Aug. 3, 2007

(87) PCT Pub. No.: WO2006/109301
PCT Pub. Date: Oct. 19, 2006

(65) Prior Publication Data
US 2011/0033521 A1    Feb. 10, 2011

Related U.S. Application Data

(60) Provisional application No. 60/671,476, filed on Apr. 15, 2005.

(51) Int. Cl.
A61K 39/00    (2006.01)
A61K 47/48    (2006.01)
A61K 38/19    (2006.01)
C07K 1/10     (2006.01)
C07K 16/46    (2006.01)

(52) U.S. Cl. .................. 424/134.1; 424/178.1; 530/351; 530/391.1; 530/402; 514/19.3

(58) Field of Classification Search ........................ None
See application file for complete search history.

(56) References Cited

U.S. PATENT DOCUMENTS

| 2002/0048786 | A1* | 4/2002 | Rosen et al. ................. 435/69.1 |
| 2003/0166870 | A1  | 9/2003 | Wu et al. |
| 2004/0147578 | A1* | 7/2004 | Calvet .......................... 514/400 |
| 2004/0223968 | A1* | 11/2004 | Charo et al. ................ 424/145.1 |

FOREIGN PATENT DOCUMENTS

| EP | 1871798 | 10/2009 |
| WO | WO 97/31949 | 4/1997 |
| WO | WO-9731949 | * 9/1997 |
| WO | WO 01/58916 | 8/2001 |
| WO | WO 2005/016226 | 2/2005 |
| WO | WO 2005/010045 | 3/2005 |
| WO | WO 2005/102391 | 3/2005 |
| WO | WO 2005/058234 | 6/2005 |
| WO | WO 2006/109301 | 10/2006 |

OTHER PUBLICATIONS

Frade et al. The Amino-terminal Domain of the CCR2 Chemokine Receptor Acts as Coreceptor for HIV-1 Infection. Journal of Clinical Investigation; vol. 100/3:497-502 (Aug. 1997).*
Hughs et al. Coevolution of the mammalian chemokines and their receptors. Immunogenetics vol. 49: 115-124 (1999).*
Communication Pursuant to Article 94(3) EPC Dated Jan. 5, 2009 From the European Patent Office Re.: Application No. 06728255.8, pp. 1-3.
Communication Pursuant to Article 94(3) EPC Dated May 14, 2008 From the European Patent Office Re.: Application No. 06728255.8, pp. 1-3.
International Preliminary Report on Patentability Dated Mar. 28, 2007 From the International Preliminary Examinin Authority Re.: Application No. PCT/IL2006/000454, pp. 1-3.
International Search Report Dated Sep. 13, 2006 From the International Searching Authority Re.: Application No. PCT/IL2006/000454, pp. 1-3.
Written Opinion Dated Sep. 13, 2006 From the International Searching Authority Re.: Application No. PCT/IL2006/000454, pp. 1-3.
Response Dated Jun. 1, 2010 to Office Action of Feb. 1, 2010 From the Israel Patent Office Re.: Application No. 186666, pp. 1-4.
Response Dated Nov. 11, 2010 to Office Action of Jul. 13, 2010 From the Israel Patent Office Re.: Application No. 186666, pp. 1-16.
Response Dated Sep. 22, 2010 to Office Action of Jun. 8, 2010 From the State Intellectual Property Office of the People's Republic of China Re. Application No. 200680012540.5, pp. 1-8.
Examination Report Dated Jul. 9, 2009 From the Instituto Mexicano de la Propriedad Industrial Re.: Application No. MC/a/2007/010484, pp. 1-4.
Response Dated Nov. 26, 2009 to Examination Report of Jul. 9, 2009 From the Instituto Mexicano de la Propriedad Industrial Re.: Application No. MX/a/2007/010484, pp. 1-4.
Datta-Mannan et al. "Chemokine-Binding Specificity of Soluble Chemokine-Receptor Analogues: Identification of Interacting Elements by Chimera Complementation", Biochemistry, 43: 14602-14611, Nov. 23, 2004. Fig.1A, 1B, 4th Receptor Mimic, p. 14603, Left Col., Concluding Remarks p. 14610.
Datta-Mannan et al. "Chemokine-Binding Specificity of Soluble Chemokine-Receptor Analogues: Identification of Interacting Elements by Chimera Complementation", Biochemistry, 43: 14602-14611, 2004. Fig.1A, 1B, 4th Receptor Mimic, p. 14603, Left Col., Concluding Remarks p. 14610.
Dana et al. "Soluble Mimics of a Chemokine Receptor: Chemokine Binding by Receptor Elements Juxtaposed on a Soluble Scaffold", Protein Science, 12(11): 2482-2491, 2003. Figs.1A-B, Protein Preparation p. 2489, Last § of Discussion.
Van Oosterhout et al. "Murine CTLA4-IgG Treatment Inhibits Airway Eosinophilia and Hyperresponsiveness and Attenuates IgE Upregulation in a Murine Model of Allergic Asthma", American Journal of Respiratory Cell and Molecular Biology, 17(3): 386-392, 1997. Material and Methods for Construction of a CTLA-IgG Fusion Protein and the Pharmacointeics Studies, p. 387.

(Continued)

*Primary Examiner* — Elizabeth C Kemmerer
*Assistant Examiner* — Regina M Deberry

(57) ABSTRACT

Molecules and compositions including same for the isolation of MCP-1 and treatment of CCR2/MCP-1 associated diseases.

4 Claims, 9 Drawing Sheets

OTHER PUBLICATIONS

Deurloo et al. "CTLA-IgG Reverses Asthma Manifestations in a Mild But Not in a More 'Severe' Ongoing Murine Model", American Journal of Respiratory Cell and Molecular Biology, 25(6): 751-760, 2001.

Monti et al. "The CC Chemokine MCP-I /CCL2 in Pancreatic Cancer Progression: Regulation of Expression and Potential Mechanisms of Antimalignant Activity", Cancer Research, 63(21): 7451-7461, 2003. End of Abstract, P.7451, Right Col., Last 8 Lines, Figs.2-3, p. 7456, p. 7460.

Jin et al. "Expression and Characterization of the Chemokine Receptor CCR2B From Rhesus Monkey", Biochemical Pharmacology, 66(2): 321-330, 2003. Fig.1.

Xu et al. "Identification of a Novel Mechanism for Endotoxin-Mediated Down-Modulation of CC Chemokine Receptor Expression", European Journal of Immunology, 30(1): 227-235, 2000. CCR2B-GFP Construct on p. 234.

Schneider et al. "In Vitro and In Vivo Properties of a Dimeric Bispecific Single-Chain Antibody IgG-Fusion Protein for Depletion of CCR2+ Target Cells in Mice", European Journal of Immunology, 35(3): 987-995, 2005.

Monteclaro et al. "The Amino-Terminal Domain of CCR2 Is Both Necessary and Sufficient for High Affinity Binding of Monocyte Chemoattractant Protein 1", The Journal of Biological Chemistry, 272(37): 23186-23190, 1997.

International Preliminary Report on Patentability Dated Mar. 28, 2007 From the International Preliminary Examininig Authority Re.: Application No. PCT/IL2006/000454, pp. 1-3.

Office Action Dated Feb. 1, 2010 From the Israel Patent Office Re.: Application No. 186666 and Its Translation Into English, pp. 1-8.

Translation of Office Action Dated Jun. 10, 2011 From the State Intellectual Property Office of the People's Republic of China Re. Application No. 200680012540.5, pp. 1-8.

Response Dated Nov. 26, 2009 to Examination Report of Jul. 9, 2009 From the Instituto Mexicano de la Propriedad Industrial Re.: Application No. MX/a/2007/010484. pp. 1-4.

Translation of Office Action dated Jun. 8, 2010 From the State Intellectual Property Office of the People's Republic of China Re. Application No. 200680012540.5, pp. 1-8.

Office Action Dated Jul. 13, 2010 From the Israel Patent Office Re.: Application No. 186666 and Its Translation Into English, pp. 1-4.

Examiner's Report Dated Jan. 5, 2012 From the Australian Government, IP Australia Re. Application No. 2006233927.

Preobrazhensky et al. "Monocyte Chemotactic Protein-1 Receptor CCR2B is a Glycoprotein That Has Tyrosine Sulfation in a Condserved Extracellular N-Terminal Region", The Journal of Immunology, 165: 5295-5303, 2000.

* cited by examiner

Figs 1a-b

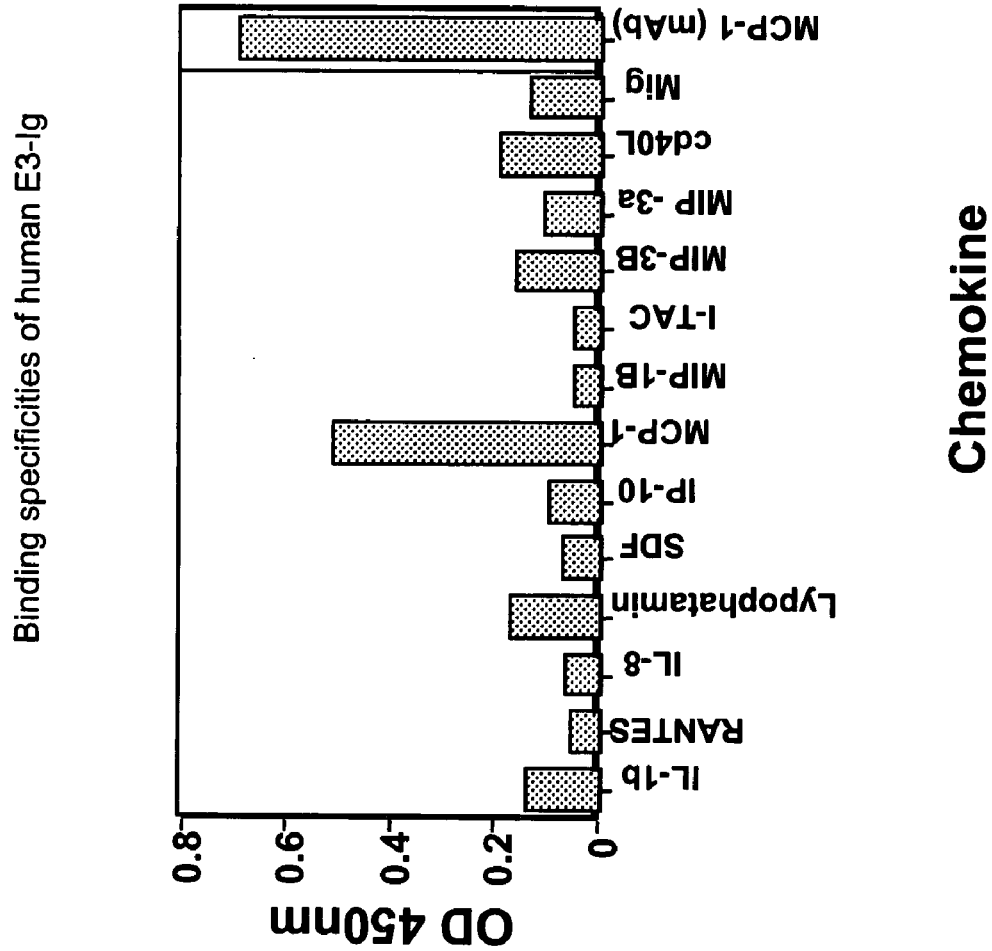

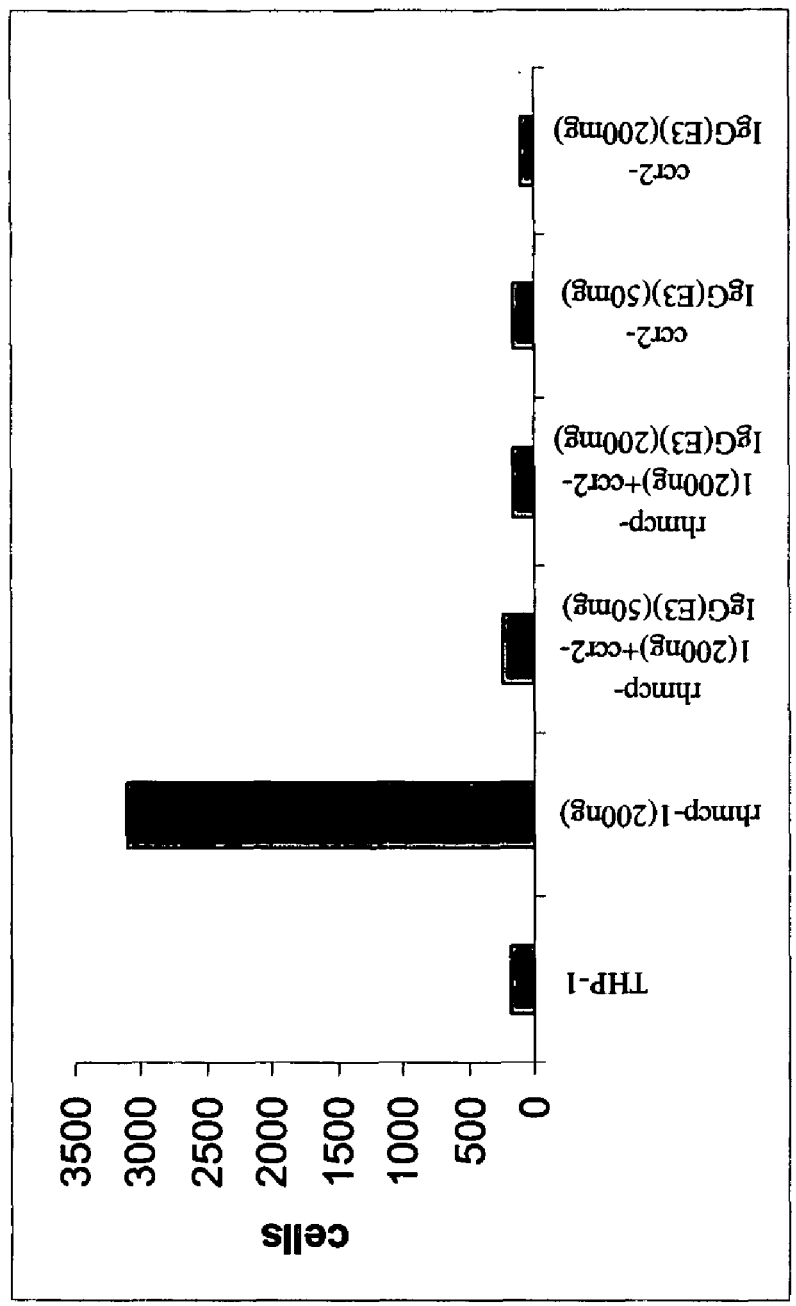

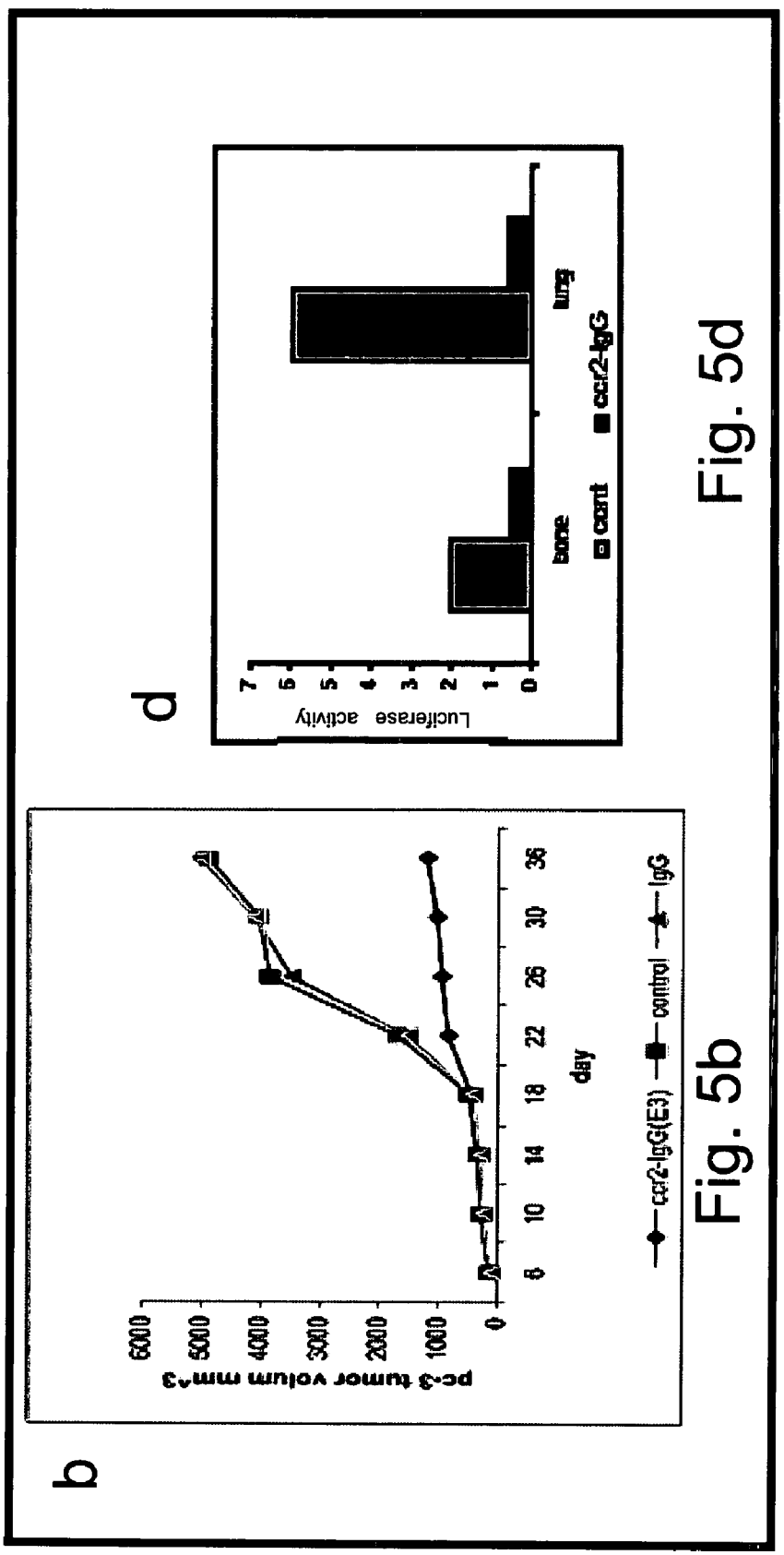

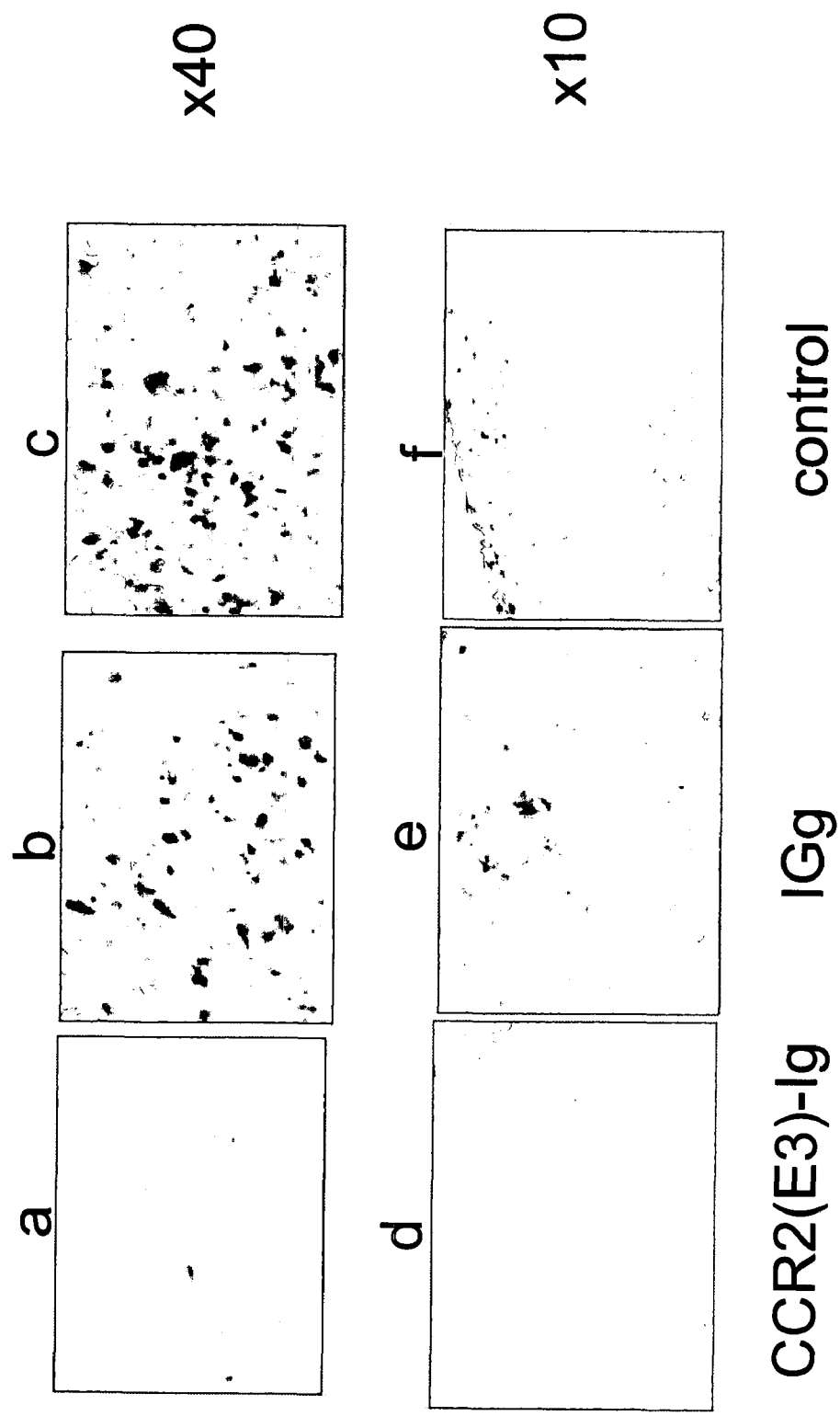
Figs 6a-f

MOLECULES AND METHODS OF USING SAME FOR TREATING MCP-1/CCR2 ASSOCIATED DISEASES

RELATED APPLICATIONS

This Application is a National Phase of PCT Patent Application No. PCT/IL2006/000454 having International Filing Date of Apr. 10, 2006, which claims the benefit of U.S. Provisional Patent Application No. 60/671,476 filed on Apr. 15, 2005. The contents of the above Applications are all incorporated herein by reference.

FIELD AND BACKGROUND OF THE INVENTION

The present invention relates to novel molecules and, more particularly, to methods of treating MCP-1/CCR2 associated diseases, such as inflammatory diseases and cancer.

Over the past several years a growing number of leukocyte chemoattractant/activating factors (chemokines) were described [Oppenheim, J. J. et al., Annu. Rev. Immunol., 9:617-648 (1991); Schall and Bacon, Curr. Opin. Immunol., 6:865-873 (1994); Baggiolini, M., et al., Adv. Immunol., 55:97-1-79 (1994)]. Chemokines are produced and secreted by a wide variety of cell types in response to early inflammatory mediators such as IL-1β or TNF-α.

The chemokine superfamily comprises two main branches: the α-chemokines (also known as the CXC chemokines) and the β-chemokines (also known as the CC chemokines). This classification is based on whether the first two cysteines in the amino acid sequence are separated by a single amino acid (CXC) or are adjacent (CC). The α-chemokine branch includes proteins such as IL-8, neutrophil activating peptide-2 (NAP-2), melanoma growth stimulatory activity (MGSA/gro or GRO α), and ENA-78, each of which have both attracting and activating effects predominantly on neutrophils and T lymphocytes. The members of the β-chemokine branch affect other blood cell types such as monocytes, lymphocytes, basophils, and eosinophils [Oppenheim, J. J. et al., Annu. Rev. Immunol., 9:617-648 (1991); Baggiolini, M., et al., Adv. Immunol., 55:97-179 (1994); Miller and Krangel, Crit. Rev. Immunol., 12:17-46 (1992); Jose, P. J., et al., J. Exp. Med., 179:881-118 (1994); Ponath, P. D., et al., J. Clin. Invest., 97:604-612 (1996)], and include proteins such as monocyte chemotactic proteins 1-4 (MCP-1, MCP-2, MCP-3, and MCP-4), RANTES, and macrophage inflammatory proteins (MIP-1α and MIP-1β).

A third smaller branch of the chemokine superfamily comprises membrane-bound chemokines. Members of this class are designated CX3C chemokines [Bazan, J. F., et al., Nature 385:640-644 (1997)].

Chemokines can mediate a range of pro-inflammatory effects on leukocytes, such as triggering of chemotaxis, degranulation, synthesis of lipid mediators, and integrin activation [Oppenheim, J. J. et al., Annu. Rev. Immunol., 9:617-648 (1991); Baggiolini, M., et al., Adv. Immunol., 55:97-179 (1994); Miller, M. D. and Krangel, M. S., Crit. Rev. Immunol., 12:17-46 (1992)].

The chemokines bind to specific cell-surface receptors belonging to the family of G-protein-coupled seven-transmembrane-domain proteins [Murphy, P. M., Annu. Rev. Immunol., 12:593-633 (1994)] which are termed "chemokine receptors". On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration.

Chemokines have been implicated as important mediators of allergic, inflammatory and autoimmune disorders and diseases, such as asthma, atherosclerosis, glomerulonephritis, pancreatitis, restenosis, rheumatoid arthritis, diabetic nephropathy, pulmonary fibrosis, and transplant rejection.

In particular, monocyte chemoattractant-1 (MCP-1), acting on its receptor CC Chemokine Receptor 2 (CCR-2), plays a role in a wide variety of indications. Upon binding to its receptor, MCP-1 induces a rapid increase in intracellular calcium concentration which leads to an increased expression of cellular adhesion molecules and eventually to cellular degranulation and the promotion of leukocyte migration.

Demonstration of the importance of the MCP-1/CCR-2 interaction has been provided by experiments with genetically modified mice. MCP-1-/- mice had normal numbers of leukocytes and macrophages, but were unable to recruit monocytes into sites of inflammation after several different types of immune challenge [Bao Lu, et al., J. Exp. Med. 1998, 187, 601]. Likewise, CCR-2-/- mice were unable to recruit monocytes or produce interferon γ when challenged with various exogenous agents; moreover, the leukocytes of CCR-2 null mice did not migrate in response to MCP-1 [Landin Boring, et al., J. Clin. Invest. 1997, 100, 2552], thereby demonstrating the specificity of the MCP-1/CCR-2 interaction. Two other groups have independently reported equivalent results with different strains of CCR-2-/- mice [William A. Kuziel, et al., Proc. Natl. Acad. Sci. USA 1997, 94, 12053, and Takao Kurihara, et al., J. Exp. Med. 1997, 186, 1757]. The viability and generally normal health of the MCP-1-/- and CCR-2-/- animals is noteworthy, in that disruption of the MCP-1/CCR-2 interaction does not induce physiological crisis. Taken together, these data suggest that molecules that block the actions of MCP-1 would be useful in treating a range of inflammatory and autoimmune disorders.

It is known that MCP-1 is upregulated in patients with rheumatoid arthritis [Alisa Koch, et al., J. Clin. Invest. 1992, 90, 772-779]. Moreover, several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats [Sawsan Youssef, et al., J. Clin. Invest. 2000, 106, 361]. Likewise, inflammatory disease symptoms could be controlled via direct administration of antibodies for MCP-1 to rats with collagen-induced arthritis [Hiroomi Ogata, et al., J. Pathol. 1997, 182, 106], or streptococcal cell wall-induced arthritis [Ralph C. Schimmer, et al., J. Immunol. 1998, 160, 1466]. Perhaps most significantly, a peptide antagonist of MCP-1, MCP-1 (9-76), was shown both to prevent disease onset and to reduce disease symptoms (depending on the time of administration) in the MRL-1 pr mouse model of arthritis [Jiang-Hong Gong, et al., J. Exp. Med. 1997, 186, 131].

MCP-1 is also upregulated in atherosclerotic lesions, and it has been shown that circulating levels of MCP-1 play a role in disease progression [Abdolreza Rezaie-Majd, et al, Arterioscler. Thromb. Vasc. Biol. 2002, 22, 1194-1199]. MCP-1 is responsible for the recruitment of monocytes into atherosclerotic areas, as shown by immunohistochemistry of macrophage-rich arterial wall [Yla-Herttuala et al., Proc Natl Acad Sci USA 88:5252-5256 (1991); Nelken et al., J Clin Invest 88:1121-1127 (1991)] and anti-MCP-1 antibody detection [Takeya et al., Human Pathol 24:534-539 (1993)]. LDL-receptor/MCP-1-deficient and apoB-transgenic/MCP-1-deficient mice show significantly less lipid deposition and macrophage accumulation throughout their aortas compared with wild-type MCP-1 strains [Alcami et al., J Immunol 160:624-633 (1998); Gosling et al., J Clin Invest 103:773-778 (1999); Gu et al., Mol. Cell. 2:275-281 (1998); Boring et al., Nature 394:894-897 (1998)].

It is known that MCP-1 is upregulated in human multiple sclerosis, and it has been shown that effective therapy with interferonβ-1β reduces MCP-1 expression in peripheral blood mononuclear cells, suggesting that MCP-1 plays a role in disease progression [Carla Iarlori, et al., J. Neuroimmunol. 2002, 123, 170-179]. Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple sclerosis. Administration of antibodies for MCP-1 to animals with EAE significantly diminished disease relapse [K. J. Kennedy, et al., J. Neuroimmunol. 1998, 92, 98]. Furthermore, two more recent reports have now shown that CCR-2-/- mice are resistant to EAE [Brian T. Fife, et al., J. Exp. Med. 2000, 192, 899; Leonid Izikson, et al., J. Exp. Med. 2000, 192, 1075].

It is known that MCP-1 is upregulated in patients who develop bronchiolitis obliterans syndrome after lung transplantation [Martine Reynaud-Gaubert, et al., J. of Heart and Lung Transplant., 2002, 21, 721-730; John Belperio, et al., J. Clin. Invest. 2001, 108, 547-556]. In a murine model of bronchiolitis obliterans syndrome, administration of an antibody to MCP-1 led to attenuation of airway obliteration; likewise, CCR2-/- mice were resistant to airway obliteration in this same model [John Belperio, et al., J. Clin. Invest. 2001, 108, 547-556]. These data suggest that antagonism of MCP-1/CCR2 may be beneficial in treating rejection of organs following transplantation.

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation [Jose-Angel Gonzalo, et al., J. Exp. Med. 1998, 188, 157]. It proved possible to reduce allergic airway inflammation in *Schistosoma mansoni* egg-challenged mice through the administration of antibodies for MCP-1 [Nicholas W. Lukacs, et al., J. Immunol. 1997, 158, 4398]. Consistent with this, MCP-1-/- mice displayed a reduced response to challenge with *Schistosoma mansoni* egg [Bao Lu, et al., J. Exp. Med. 1998, 187, 601].

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen [Clare M. Lloyd, et al., J. Exp. Med. 1997, 185, 1371]. In addition, MCP-1-/- mice with induced nephrotoxic serum nephritis showed significantly less tubular damage than their MCP-1+/+ counterparts [Gregory H. Tesch, et al., J. Clin. Invest. 1999, 103, 73].

One study has demonstrated the potential therapeutic value of antagonism of the MCP-1/CCR2 interaction in treating systemic lupus erythematosus. Crossing of MCP-1-/- mice with MRL-FAS.sup.1pr mice—the latter having a fatal autoimmune disease that is analogous to human systemic lupus erythematosus-results in mice with less disease and longer survival than the wildtype MRL-FAS.sup.1pr mice [Gregory H. Tesch, et al., J. Exp. Med. 1999, 190, 1813].

The MCP-1/CCR2 interaction in also relevant in pathology of colitis as CCR-2-/- mice were protected from the effects of dextran sodium sulfate-induced colitis [Pietro G. Andres, et al., J. Immunol. 2000, 164, 6303].

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated [Michael L. Jones, et al., J. Immunol. 1992, 149, 2147].

The MCP-1/CCR2 interaction is also relevant in cancer. When immunodeficient mice bearing human breast carcinoma cells were treated with an anti-MCP-1 antibody, inhibition of lung micrometastases and increases in survival were observed [Rosalba Salcedo, et al., Blood 2000, 96, 34-40]. In particular MCP-1 is indicated in prostate cancer as described in details in PCT WO 2004/080273 to the present inventors.

Restinosis is yet another indication in which MCP-1 is involved. Mice deficient in CCR2 showed reductions in the intimal area and in the intima/media ratio (relative to wildtype littermates) after injury of the femoral artery [Merce Roque, et al. Arterioscler. Thromb. Vasc. Biol. 2002, 22, 554-559).

Other studies have provided evidence that MCP-1 is overexpressed in various disease states not mentioned above. These reports provide correlative evidence that MCP-1 antagonists could be useful therapeutics for such diseases. MCP-1 has been shown to be overexpressed in the intestinal epithelial cells and bowel mucosa of patients with inflammatory bowel disease [H. C. Reinecker, et al., Gastroenterology 1995, 108, 40; Michael C. Grimm, et al., J. Leukoc. Biol. 1996, 59, 804]. Two reports describe the overexpression of MCP-1 rats with induced brain trauma [J. S. King, et al., J. Neuroimmunol. 1994, 56, 127; Joan W. Berman, et al., J. Immunol. 1996, 156, 3017]. MCP-1 has also been shown to be overexpressed in rodent cardiac allografts, suggesting a role for MCP-1 in the pathogenesis of transplant arteriosclerosis [Mary E. Russell, et al. Proc. Natl. Acad. Sci. USA 1993, 90, 6086]. The overexpression of MCP-1 has been noted in the lung endothelial cells of patients with idiopathic pulmonary fibrosis [Harry N. Antoniades, et al., Proc. Natl. Acad. Sci. USA 1992, 89, 5371]. Similarly, the overexpression of MCP-1 has been noted in the skin from patients with psoriasis [M. Deleuran, et al., J. Dermatol. Sci. 1996, 13, 228, and R. Gillitzer, et al., J. Invest. Dermatol. 1993, 101, 127]. Finally, a recent report has shown that MCP-1 is overexpressed in the brains and cerebrospinal fluid of patients with HIV-1-associated dementia [Alfredo Garzino-Demo, WO 99/46991].

Most chemokine antagonists reported to date are either neutralizing antibodies to specific chemokines or small molecule antagonists [Howard et al., Trend Biotechnol 14:46-51 (1996)].

Anti-MCP-1 antibodies have been used effectively in a number of mouse disease models as described above. However, a major problem associated with using antibodies to antagonize chemokine function is that they must be humanized before use in chronic human diseases. Furthermore, the ability of multiple chemokines to bind and activate a single receptor forces the development of a multiple antibody strategy or the use of cross-reactive antibodies in order to completely block or prevent pathological conditions.

Several small molecule antagonists of chemokine receptor function have been reported in the scientific and patent literature [White, J Biol Chem 273:10095-10098 (1998); Hesselgesser, J Biol Chem 273:15687-15692 (1998); Bright et al., BioorgMed Chem Lett 8:771-774 (1998); Lapierre, 26th Natl Med Chem Symposium, June 14-18, Richmond (Va.), USA (1998); Forbes et al., Bioorg Med Chem Lett 10:1803-18064 (2000); Kato et al., WO 97/24325; Shiota et al., WO 97/44329; Naya et al., WO 98/04554; Takeda Industries, JP 09-55572 (1998); Schwender et al., WO 98/02151; Hagmann et al., WO 98/27815; Connor et al., WO 98/06703; Wellington et al., U.S. Pat. No. 6,288,103]. The specificity of the chemokine receptor antagonists, however, suggests that inflammatory disorders characterized by multiple or redundant chemokine expression profiles will be relatively more refractory to treatment by these agents.

There is thus a widely recognized need for, and it would be highly advantageous to have, compositions and methods using same for treating CCR-2 associated diseases which are devoid of the above limitations.

SUMMARY OF THE INVENTION

According to one aspect of the present invention there is provided a molecule comprising a heterologous amino acid sequence conjugated to a CCR2 amino acid sequence devoid of an N-terminus domain of CCR2, the CCR2 amino acid sequence being capable of binding MCP-1, and wherein the molecule is non immunogenic.

According to another aspect of the present invention there is provided a molecule comprising a CCR2 amino acid sequence attached to a non-proteinaceous moiety, wherein the CCR2 amino acid sequence is capable of binding MCP-1 and whereas the molecule is non-immunogenic in a subject.

According to yet another aspect of the present invention there is provided a molecule comprising at least two CCR2 amino acid sequences each being capable of binding MCP-1.

According to still another aspect of the present invention there is provided a molecule comprising a tag attached to a CCR2 amino acid sequence devoid of an N-terminus domain of CCR2, the CCR2 amino acid sequence being capable of binding MCP-1.

According to an additional aspect of the present invention there is provided a molecule as set forth in SEQ ID NO: 14 or 15.

According to yet an additional aspect of the present invention there is provided the pharmaceutical composition comprising the molecule and a pharmaceutically acceptable carrier.

According to still an additional aspect of the present invention there is provided a pharmaceutical composition comprising a molecule which comprises a CCR2 amino acid sequence devoid of an N-terminus domain of CCR2 and being capable of binding an MCP-1 and a pharmaceutically acceptable carrier, the pharmaceutical composition being non-immunogenic.

According to a further aspect of the present invention there is provided a method of treating an MCP-1/CCR2 associated disease in a subject in need thereof, comprising administering to the subject a therapeutically effective amount of the molecule, thereby treating the MCP-1/CCR2 associated disease in the subject.

According to yet a further aspect of the present invention there is provided use of the molecule for the manufacture of a medicament identified for treating an MCP-1/CCR2 associated diseases.

According to still a further aspect of the present invention there is provided a method of isolating MCP-1 from a biological sample, the method comprising: (a) contacting the biological sample with the molecule of claim 4 such that MCP-1 and the molecule of claim 4 form a complex; and (b) isolating the complex to thereby isolate MCP-1 from the biological sample.

According to still a further aspect of the present invention there is provided a method of treating an MCP-1/CCR2 associated disease in a subject in need thereof, comprising administering to the subject a therapeutically effective amount of a molecule which comprises a CCR2 amino acid sequence devoid of an N-terminus domain of CCR2 and being capable of binding an MCP-1, thereby treating the MCP-1/CCR2 associated disease in the subject.

According to still a further aspect of the present invention there is provided use of a molecule which comprises a CCR2 amino acid sequence devoid of an N-terminus domain of CCR2 and being capable of binding an MCP-1, for the manufacture of a medicament identified for treating an MCP-1/CCR2 associated diseases.

According to further features in preferred embodiments of the invention described below, the heterologous amino acid sequence comprises an immunoglobulin amino acid sequence.

According to still further features in the described preferred embodiments the CCR2 amino acid sequence devoid of an N-terminus domain of CCR2 is as set forth in SEQ ID NO: 2.

According to still further features in the described preferred embodiments the MCP-1/CCR2 associated disease is selected from the group consisting of inflammatory diseases, necrosis, atherosclerosis, cancer, multiple sclerosis, atheroma, monocytic leukemia, kidney diseases (e.g., glomerularnephritis), hamman-rich syndrome, endometriosis, rheumatoid arthritis, bronchiolitis, asthma, systemic lupus erythematosus, inflammatory bowel diseases (e.g., colitis), alveolitis, restinosis, brain trauma, psoriasis, idiopathic pulmonary fibrosis and transplant arteriosclerosis.

According to still further features in the described preferred embodiments the tag is an epitope tag.

According to still further features in the described preferred embodiments the molecule is attached to a solid support.

According to still further features in the described preferred embodiments the molecule is attached to a non-proteinaceous moiety.

According to still further features in the described preferred embodiments the non-proteinaceous moiety is selected from the group consisting of polyethylene glycol (PEG), Polyvinyl pyrrolidone (PVP), poly(styrene comaleic anhydride) (SMA), and divinyl ether and maleic anhydride copolymer (DIVEMA).

According to still further features in the described preferred embodiments the pharmaceutically acceptable carrier is formulated for parenteral administration.

According to still further features in the described preferred embodiments the pharmaceutically acceptable carrier is substantially non-immunogenic.

According to still further features in the described preferred embodiments the pharmaceutically acceptable carrier comprises a lipoamine acid.

According to still further features in the described preferred embodiments the pharmaceutically acceptable carrier comprises a carbohydrate.

According to still further features in the described preferred embodiments the pharmaceutically acceptable carrier comprises a microsphere.

According to still further features in the described preferred embodiments the pharmaceutically acceptable carrier comprises a liposome.

According to still further features in the described preferred embodiments the pharmaceutically acceptable carrier comprises a polymer microsphere.

The present invention successfully addresses the shortcomings of the presently known configurations by providing novel molecules and methods using same for treating MCP-1/CCR2 associated diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 1a—Human sera from 23 prostate cancer patients, 21 patients with Benign Prostatic Hyperplasia (BPH) and 10 control subjects, all age-matched mails, were monitored for possible appearance of autoantibodies to the following 13 chemokines: SDF-1 (CXCL12, GenBank Accession No. NM199168), MIF (GenBank Accession No. L19686), MIP-1α (CCL3, GenBank Accession No. NM002983), MIP-1β (CCL4, GenBank Accession No. NM002984), IL-8 (CXCL8, GenBank Accession No. M2813), IP-10 (CXCL10, GenBank Accession No. NM001565), MIP-3α (CCL20, GenBank Accession No. BC020698), MIP-3β (CCL-19, GenBank Accession No. BC027968), Lymphotactin (XCL1, GenBank Accession No. NM002995), MIG (CXCL9, GenBank Accession No. NM002416), RANTES (CCL5, GenBank Accession No. NM002985), MCP-3 (CCL7, GenBank Accession No. NM006273) and MCP-1 (CCL2, GenBank Accession No. NM002982). A significant antibody titer ($p<0.01$) was observed in a vast majority of prostate cancer patients to only one of the above chemokines, MCP-1. FIG. 1b—$Log_2$Ab titer to MCP-1 in each of the clinical samples described in FIG. 1a, above. About 82% of prostate cancer patients (19/23) and only about 4.7% (1/21) of those with BPH displayed a significant (log 2Ab titer>10) response to MCP-1 ($p<0.01$).

FIG. 3 is a bar graph depicting specific binding of the E3 domain of CCR2 to MCP-1.

FIG. 4 is a bar graph depicting the ability of human CCR2 (E3)-IgG to inhibit MCP-1 induced migration of THP-1 cells (ATCC Accession NO. TIB-202). An in vitro transwell migration assay was performed. In brief, THP-1 cells ($10^6$/well) were added to the upper chamber of the transwell plate and CCL2 (recombinant human MCP-1, RHMCP-1; (20 ng/ml) was added to the lower well, that was also supplemented with different concentrations of CCR2(E3)-IgG as shown in the Figure. Following 2 hours of incubation at 37° C. migrating THP-1 cells were counted by a FACS. Result are shown as mean of triplicates±SE.

FIGS. 5a-d are graphs depicting the development of primary tumor and its metastatic spread as compared between CCR2(E3)-IgG administered cells and control (IgG administered or PBS treated) cells. FIGS. 5a-b are a graphs depicting the ability of CCR2(E3)-IgG to reduce tumor growth through time either when administration of CCR2(E3)-IgG starts together with (FIG. 5a), or 18 days after (FIG. 5b) administration of PC-3 cells. Tumor volume ($mm^3$) of tumors from CCR2(E3)-IgG administered (depicted in blue), isotype matched control IgG administered (depicted in green), or PBS administered (depicted in brown or yellow) mice was measured repeatedly in various times as indicated. FIG. 5c is a graph showing the anti-tumor activity of CCR2(E3)-IgG injected 8 days following PC3 cells administration. The volume ($mm^3$) of tumors from mice administered with PC-3 cells together with CCR2(E3)-IgG (depicted in blue), isotype matched control IgG administered (depicted in green), or PBS (depicted in pink) was measured repeatedly in various times as indicated. These results support the preventive and therapeutic activity of CCR2(E3)-IgG shown in FIGS. 5a-b. FIG. 5d is a bar graph depicting inhibition of bone and lung metastasis of luciferase expressing PC-3 cells by CCR2(E3)-Ig as indicated, with comparison to control cells.

FIGS. 6a-f are photographs showing that blockage of CCL-2 with CCR2(E3)-Ig entirely suppresses VEGF production at the tumor site. Treatment with either CCR2(E3)-Ig (FIGS. 6a,d), isotype matched control IgG (FIGS. 6b,e) or PBS (control cells; FIGS. 6c,f), is shown. Animals were sacrificed and tumor/tissue withdrawn. Tissues were washed, fixed, and permeabilized, and VEGF was detected by immunostaining using confocal microscopy. Micrographs are shown either in X 10 (FIGS. 6a-c) or X 40 (FIGS. 6d-f) magnification.

DESCRIPTION OF THE PREFERRED EMBODIMENTS

Figure 1:
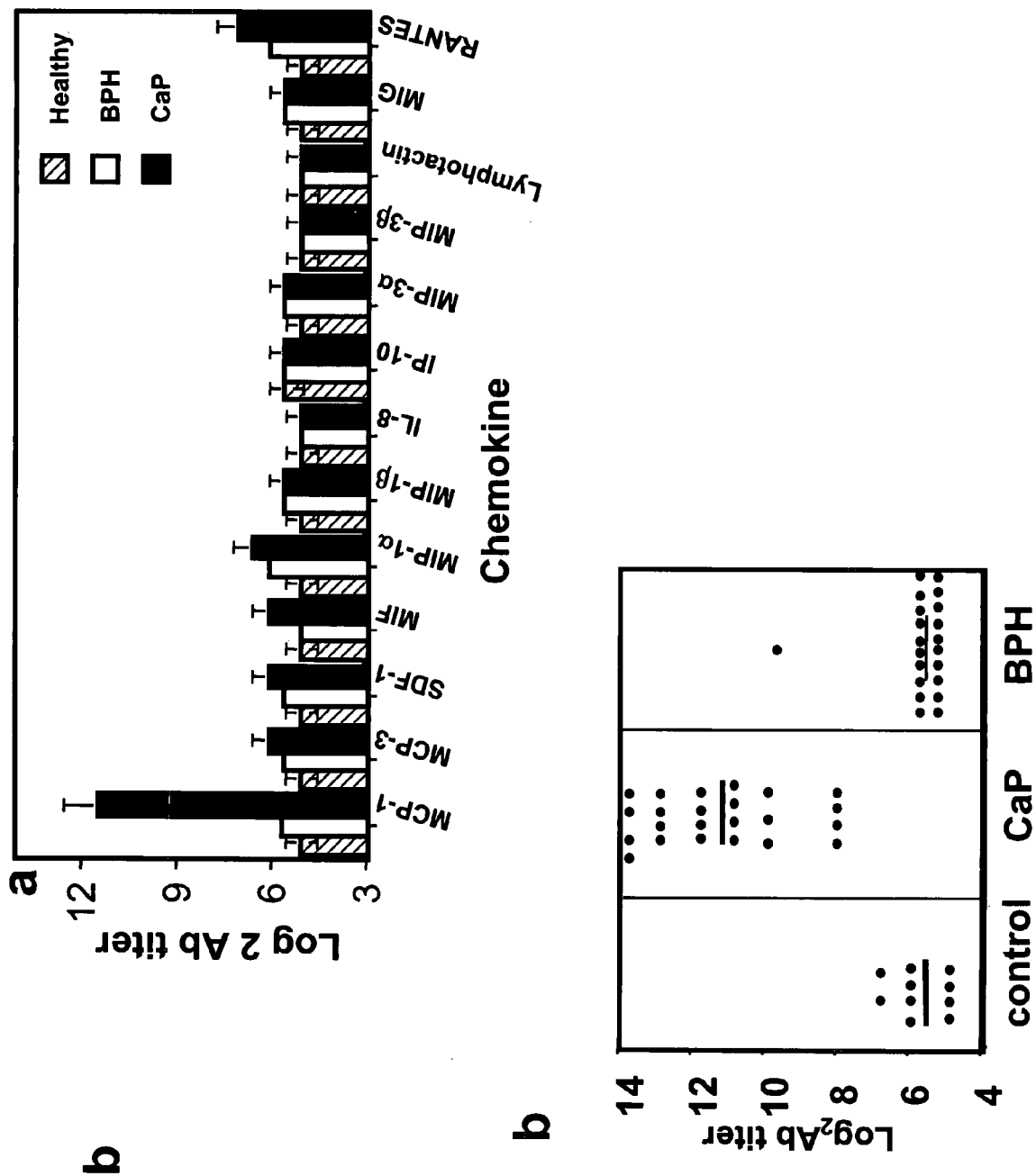
FIGS. 1a-b are graphs showing that prostate cancer patients selectively develop a highly significant autoantibody titer against MCP-1.

The present invention is of molecules, compositions including same and methods of using same for treating MCP-1/CCR2 associated diseases, such as cancer.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Monocyte chemoattractant protein (MCP)-1, also termed CCL2, specifically attracts monocytes and memory T cells. Its expression occurs in a variety of diseases characterized by cell migration, and there is substantial biological and genetic evidence for its essential role in cancer, cardiovascular diseases and inflammatory diseases. Despite intensive screening, there are, as yet, no antagonists of the receptor of MCP-1/CCL2, CCR2.

While reducing the present invention to practice, the present inventors uncovered that binding of MCP-1 to CCR2 is exclusively mediated by the third extracellular region (E3) of CCR2 (amino acid coordinates 273-292 of GenBank Accession No. NP_000639.1). This is in sharp contrast to previous report by Datta Mannan and Stone [Datta-Mannan And Stone (2004) Biochemistry 43:14602-11] who showed that MCP-1 binding to CCR2 is dependent on both the N-terminal region (N-ter) and third extracellular loop (E3) of CCR2. These results suggest that peptides comprising the E3 region of CCR2 may be used as inhibitory agents, by essentially sequestering MCP-1.

Thus, the present invention envisages the use of any CCR2 amino acid sequence which comprises the E3 domain of CCR2 and preferably devoid of an N-terminus domain of CCR2, and/or compositions comprising same for the treatment of MCP-1/CCR2 associated diseases, such as cancer. Importantly, compositions of the present invention are non-immunogenic to achieve maximal therapeutic efficacy. Thus, the present invention envisages for example, inclusion of the CCR2 sequence in a complex where it is attached to a proteinaceous (e.g., heterologous amino acid sequence) or non-proteinaceous moieties (e.g., PEG), each of which being capable of prolonging the half-life of the composition in the circulation.

Thus, according to one aspect of the present invention there is provided a non-immunogenic molecule comprising at least one heterologous amino acid sequence conjugated to a CCR2 amino acid sequence preferably devoid of an N-terminus domain of CCR2 (e.g., amino acid coordinates 1-41 of translated GenBank Accession No. NM_000647/NP_000638 or corresponding amino acid coordinates of GenBank Accession No. NM_000648/NP_000639), the CCR2 amino acid sequence being capable of binding MCP-1.

As shown in the Examples section which follows, chimeric molecules of this aspect of the present invention which comprise the newly uncovered MCP-1 binding domain (E3-IgG), inhibited tumor development even as long as 18 days following tumor cell administration. Surprisingly, the same chimeric molecules even dramatically inhibited tumor metastasis to bone and lung tissues. Altogether, the present findings support the use of the molecules of the present invention in the treatment of MCP-1/CCR2 associated diseases, such as cancer.

It should be noted that chimeric molecules of this aspect of the present invention are markedly different from those describes in WO 97/31949 which teaches the use of chimeric-E3 (i.e., KLH-E3) peptides for the production of antibodies directed at the E3 region of CCR2, thereby inhibiting the CCR2 receptor from ligand binding. The non-immunogenic peptides of the present invention are used for targeting the ligand of CCR2, MCP-1, to thereby inhibit the ligand from receptor binding. Thus, molecules of the present invention allow exquisite therapeutic control and specificity, they can be easily synthesized and administered and are featured by high bioavailability.

As used herein MCP-1 interchangeably referred to CCL2, refers to a mammalian (e.g., human) MCP-1 protein such as set forth in GenBank Accession Nos. NM_002982 or NP_002973.

As used herein the term "non-immunogenic" refers to a substance which is substantially incapable of producing an immune response in a subject administered therewith. For example, non-immunogenic in a human means that upon contacting the chimeric molecule of this aspect of the present invention with the appropriate tissue of a human, no state of sensitivity or resistance to the chimeric molecule is demonstrable upon the second administration of the chimeric molecule after an appropriate latent period (e.g., 8 to 14 days).

As used herein "CCR2 amino acid sequence" refers to a peptide portion of a mammalian (e.g., human) chemokine C—C receptor 2 protein having affinity binding for MCP-1. It should be noted that a single CCR2 amino acid sequence may be included in the molecules of the present invention, but inclusion of at least two CCR2 amino acid sequences, each being capable of binding CCR2 (preferably with high affinity, e.g., SEQ ID NO: 9) may be preferred. Due to increased avidity, these polypeptides may be used as potent inhibitors of MCP-1 activity and lower dosages may be administered.

As used herein "affinity binding" refers to a minimal $K_D$ value of at least $10^{-6}$ M.

Examples of CCR2 proteins are provided in GenBank Accession Nos. NM_000647 and NP_000639.1. As mentioned the CCR2 of this aspect of the present invention is preferably devoid of an N-terminus domain, but retains an E3 domain (i.e., amino acid coordinates 273-292 of GenBank Accession No. NM_000647, SEQ ID NO: 2) or mimetics thereof.

As used herein the term "mimetics" when made in reference to peptides refers to molecular structures, which serve as substitutes for the peptides of the present invention in interaction with MCP-1 [Morgan et al. (1989) Ann. Reports Med. Chem. 24:243-252 for a review of peptide mimetics].

Peptide mimetics, as used herein, include synthetic structures (known and yet unknown), which may or may not contain amino acids and/or peptide bonds, but retain the structural and functional features of a peptide ligand. Types of amino acids which can be utilized to generate mimetics are further described hereinbelow. The term, "peptide mimetics" also includes peptoids and oligopeptoids, which are peptides or oligomers of N-substituted amino acids [Simon et al. (1972) Proc. Natl. Acad. Sci. USA 89:9367-9371]. Further included as peptide mimetics are peptide libraries, which are collections of peptides designed to be of a given amino acid length and representing all conceivable sequences of amino acids corresponding thereto. Methods for the production of peptide mimetics are described hereinbelow.

According to a preferred embodiment of this aspect of the present invention, the CCR2 amino acid sequence includes the amino acid sequence of SEQ ID NO: 2 and can be encoded by a nucleic acid sequence set forth by SEQ ID NO: 1.

According to another preferred embodiment of this aspect of the present invention, the molecule of this aspect of the present invention is as set forth in SEQ ID NO: 14 or 15.

The term "peptide" as used herein encompasses native peptides (either degradation products, synthetically synthesized peptides or recombinant peptides) and as mentioned hereinabove, peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |

TABLE 2-continued

| Non-conventional amino acid | Code | Non-conventional amino acid | Code |
|---|---|---|---|
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchex | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchex | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the present peptides are preferably utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclicization does not severely interfere with peptide characteristics, cyclic forms of the peptide can also be utilized.

Generation of peptide mimetics, as described hereinabove, can be effected using various approaches, including, for example, display techniques.

Thus, the present invention contemplates a display library comprising a plurality of display vehicles (such as phages, viruses or bacteria) each displaying at least 2, at least 3, at least 5, at least 7, at least 11, at least 15 consecutive amino acids derived from polypeptide sequences of the E3 of CCR2 (e.g., SEQ ID NO: 2).

Methods of constructing such display libraries are well known in the art. Such methods are described in, for example, Young A C, et al., "The three-dimensional structures of a polysaccharide binding antibody to *Cryptococcus neoformans* and its complex with a peptide from a phage display library: implications for the identification of peptide mimotopes" J Mol Biol 1997 Dec. 12; 274(4):622-34; Giebel L B et al. "Screening of cyclic peptide phage libraries identifies ligands that bind streptavidin with high affinities" Biochemistry 1995 Nov. 28; 34(47):15430-5; Davies E L et al., "Selection of specific phage-display antibodies using libraries derived from chicken immunoglobulin genes" J Immunol Methods 1995 Oct. 12; 186(1):125-35; Jones C R T al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Peptide mimetics can also be uncovered using computational biology. Software programs useful for displaying three-dimensional structural models, such as RIBBONS (Carson, M., 1997. Methods in Enzymology 277, 25), O (Jones, T A. et al., 1991. Acta Crystallogr. A47, 110), DINO (DINO: Visualizing Structural Biology (2001) http://www.dino3d.org); and QUANTA, INSIGHT, SYBYL, MACROMODE, ICM, MOLMOL, RASMOL and GRASP (reviewed in Kraulis, J., 1991. Appl Crystallogr. 24, 946) can be utilized to model interactions between MCP-1 and prospective peptide mimetics to thereby identify peptides which display the highest probability of binding to a specific MCP-1 region. Computational modeling of protein-peptide interactions has been successfully used in rational drug design, for further detail, see Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109, and Mauro M J. et al., 2002. J Clin Oncol. 20, 325-34.

As mentioned the chimeric molecule of this aspect of the present invention includes a heterologous amino acid sequence.

As used herein the phrase "heterologous amino acid sequence" refers to a non-immunogenic amino acid sequence which does not form a part of the CCR2 amino acid sequence. This sequence preferably confers solubility to the molecule of this aspect of the present invention, preferably increasing the half-life of the chimeric molecule in the serum.

The heterologous amino acid sequence is generally localized at the amino- or carboxyl-terminus of the CCR2 peptide of the present invention.

As mentioned, the at least one heterologous amino acid sequence can be conjugated to the CCR2 amino acid sequence of the present invention. For example, the at least one CCR2 amino acid sequence may be embedded between two heterologous sequences, such as described Hoogenboom (1991) Mol. Immunol. 28:1027-1037. The heterologous amino acid sequence may be attached to the CCR2 amino acid sequence by any of peptide or non-peptide bond. Attachment of the CCR2 amino acid sequence to the heterologous amino acid sequence may be effected by direct covalent bonding (peptide bond or a substituted peptide bond) or indirect binding such as by the use of a linker having functional groups. Functional groups include, without limitation, a free carboxylic acid (C(=O)OH), a free amino group (NH$_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl).

An example of a heterologous amino acid sequence which may be used in accordance with this aspect of the present invention is an immunoglobulin sequence, such as the hinge and Fc regions of an immunoglobulin heavy domain (see U.S. Pat. No. 6,777,196). The immunoglobulin moiety in the chimeras of this aspect of the present invention may be obtained from IgG1, IgG2, IgG3 or IgG4 subtypes, IgA, IgE, IgD or IgM, as further discussed herein below.

Chimeras constructed from a receptor sequence linked to an appropriate immunoglobulin constant domain sequence (immunoadhesins) are known in the art. Immunoadhesins reported in the literature include fusions of the T cell receptor [Gascoigne et al., Proc. Natl. Acad. Sci. USA, 84: 2936-2940 (1987)]; CD4 [Capon et al., Nature 337: 525-531 (1989); Traunecker et al., Nature, 339: 68-70 (1989); Zettmeissl et al., DNA Cell Biol. USA, 9: 347-353 (1990); Byrn et al., Nature, 344: 667-670 (1990)]; L-selectin (homing receptor) [(Watson et al., J. Cell. Biol., 110:2221-2229 (1990); Watson et al., Nature, 349: 164-167 (1991)]; CD44 [Aruffo et al., Cell, 61: 1303-1313 (1990)]; CD28 and B7 (Linsley et al., J. Exp. Med., 173: 721-730 (1991)]; CTLA-4 [Lisley et al., J. Exp. Med. 174: 561-569 (1991)]; CD22 [Stamenkovic et al., Cell, 66:1133-1144 (1991)]; TNF receptor [Ashkenazi et al., Proc. Natl. Acad. Sci. USA, 88: 10535-10539 (1991); Lesslauer et al., Eur. J. Immunol., 27: 2883-2886 (1991); Peppel et al., J. Exp. Med., 174:1483-1489 (1991)]; NP receptors [Bennett et al., J. Biol. Chem. 266:23060-23067 (1991)]; and IgE receptor α [Ridgway et al., J. Cell. Biol., 1 15:abstr. 1448 (1991)].

Typically, in such fusions the chimeric molecule will retain at least functionally active hinge and CH2 and CH3 domains of the constant region of an immunoglobulin heavy chain. Fusions can also be generated to the C-terminus of the Fc portion of a constant domain, or immediately N-terminal to the CH1 of the heavy chain or the corresponding region of the light chain.

The exact site at which fusion (conjugation) between the heterologous sequence and the CCR2 amino acid sequence is not critical. Particular sites are well known in the art and may be selected in order to optimize the biological activity, secretion or binding characteristics of the chimeric molecules of this aspect of the present invention (see Example 3 of the Example section which follows).

Though it may be possible to conjugate the entire heavy chain constant region to the CCR2 amino acid sequence of the present invention, it is preferable to fuse shorter sequences. For example, a sequence beginning in the hinge region just upstream of the papain cleavage site, which defines IgG Fc chemically; residue 216, taking the first residue of heavy chain constant region to be 114, or analogous sites of other immunoglobulins, is used in the fusion. In a particularly preferred embodiment, the CCR2 amino acid sequence is fused to the hinge region and CH2 and CH3, or to the CH1, hinge, CH2 and CH3 domains of an IgG1, IgG2, or IgG3 heavy chain (see U.S. Pat. No. 6,777,196). The precise site at which the fusion is made is not critical, and the optimal site can be determined by routine experimentation.

As mentioned, the immunoglobulin sequences used in the construction of the chimeric molecules of this aspect of the present invention may be from an IgG immunoglobulin heavy chain constant domain. The use of human IgG 1 and IgG3 immunoglobulin sequences is preferred. A major advantage of using IgG1 is that IgG1 can be purified efficiently on immobilized protein A. In contrast, purification of IgG3 requires protein G, a significantly less convenient medium. However, other structural and functional properties of immunoglobulins should be considered when choosing the Ig fusion partner for a particular chimera construction. For example, the IgG3 hinge is longer and more flexible, so it can accommodate larger CCR2 amino acid sequences that may not fold or function properly when fused to IgG1. Another consideration may be valency; IgG are bivalent homodimers, whereas Ig subtypes like IgA and IgM may give rise to dimeric or pentameric structures, respectively, of the basic Ig homodimer unit. Other considerations in selecting the immunoglobulin portion of the chimeric molecules of this aspect of the present invention are described in U.S. Pat. No. 6,77,196.

Thus, molecules of this aspect of the present invention may comprise a heterologous amino acid sequence, as described above.

Additionally or alternatively as mentioned hereinabove CCR2 amino acid sequences (capable of binding MCP-1) of the present invention may be attached to a non-proteinaceous moiety, such molecules are selected non-immunogenic in a subject. Such a molecule is highly stable (resistant to in-vivo proteaolytic activity probably due to steric hindrance conferred by the non-preoteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation as further described hereinbelow).

As mentioned, the CCR2 amino acid sequence is attached to a non-proteinaceous moiety. The phrase "non-proteinaceous moiety" as used herein refers to a molecule not including amino acids (peptide bonded) that is attached to the above-described CCR2 amino acid sequence. According to presently preferred embodiments the non-proteinaceous moiety of this aspect of the present invention is a polymer or a co-polymer (synthetic or natural). Non-limiting examples of the non-proteinaceous moiety of the present invention include polyethylene glycol (PEG), Polyvinyl pyrrolidone (PVP), divinyl ether and maleic anhydride copolymer (DIVEMA; see for example, Kaneda Y, et al., 1997, Biochem. Biophys. Res. Commun. 239: 160-5) and poly(styrene comaleic anhydride) (SMA; see for example, Mu Y, et al., 1999, Biochem Biophys Res Commun. 255: 75-9).

Bioconjugation of such a non-proteinaceous moiety confers the CCR2 amino acid sequence with stability (e.g., against protease activities) and/or solubility (e.g., within a biological fluid such as blood, digestive fluid) while preserving its biological activity and prolonging its half-life. Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the CCR2 amino acid sequence of the present invention (i.e., MCP-1 binding).

Bioconjugation of the CCR2 amino acid sequence with PEG (i.e., PEGylation) can be effected using PEG derivatives such as N-hydroxysuccinimide (NHS) esters of PEG carboxylic acids, monomethoxyPEG$_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsvlle, Ala.)]. If desired, many of the above derivatives are available in a monofunctional monomethoxyPEG (mPEG) form. In general, the PEG added to the CCR2 amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Conveniently, PEG can be attached to a chosen position in the CCR2 amino acid sequence by site-specific mutagenesis as long as the activity of the conjugate is retained (i.e., MCP-1 binding). For example, the Cysteine residue at position 5 of the CCR2 amino acid sequence as set forth in SEQ ID NO:1 can be a target for PEGylation. Additionally or alternatively, other Cysteine residues can be added to the CCR2 amino acid sequence (e.g., at the N-terminus or the C-terminus) to thereby serve as a target for PEGylation. Computational analysis may be effected to select a preferred position for mutagenesis without compromising the activity.

Various conjugation chemistry of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1:NaH 5:divinyl sulfone 50, at 0.2 gram PEG/mL DCM). PEG-AC is made under argon by reacting a DCM solution of the PEG- OH with acryloyl chloride and triethylamine (molar ratios: OH 1:acryloyl chloride 1.5:triethylamine 2, at 0.2 gram PEG/mL DCM). Such chemical groups can be attached to linearized, 2-arm, 4-arm, or 8-arm PEG molecules.

While conjugation to cysteine residues is one convenient method by which the CCR2 amino acid of the present invention can be PEGylated, other residues can also be used if desired. For example, acetic anhydride can be used to react with $NH_2$ and SH groups, but not COOH, S—S, or —$SCH_3$ groups, while hydrogen peroxide can be used to react with —SH and —$SCH_3$ groups, but not $NH_2$. Reactions can be conducted under conditions appropriate for conjugation to a desired residue in the peptide employing chemistries exploiting well-established reactivities.

For bioconjugation of the CCR2 amino acid sequence of the present invention with PVP, the terminal COOH-bearing PVP is synthesized from N-vinyl-2-pyrrolidone by radical polymerization in dimethyl formamide with the aid of 4,4'-azobis-(4-cyanovaleric acid) as a radical initiator, and 3-mercaptopropionic acid as a chain transfer agent. Resultant PVPs with an average molecular weight of Mr 6,000 can be separated and purified by high-performance liquid chromatography and the terminal COOH group of synthetic PVP is activated by the N-hydroxysuccinimide/dicyclohexyl carbodiimide method. The CCR2 amino acid sequence is reacted with a 60-fold molar excess of activated PVP and the reaction is stopped with amino caploic acid (5-fold molar excess against activated PVP), essentially as described in Haruhiko Kamada, et al., 2000, Cancer Research 60: 6416-6420, which is fully incorporated herein by reference.

Resultant conjugated CCR2 molecules (e.g., PEGylated or PVP-conjugated CCR2) are separated, purified and qualified using e.g., high-performance liquid chromatography (HPLC). In addition, purified conjugated molecules of this aspect of the present invention may be further qualified using e.g., in vitro assays in which the binding specificity of MCP-1 to its receptor (e.g., CCR2) is tested in the presence or absence of the CCR2 conjugates of the present invention, essentially as described for other chemokines [e.g., MIP-1α, see for example, Hesselgesser J, 1998 (Supra), which is fully incorporated herein by reference].

Molecules of this aspect of present invention can be biochemically synthesized such as by using standard solid phase techniques. These methods include exclusive solid phase synthesis, partial solid phase synthesis methods, fragment condensation and classical solution synthesis. These methods are preferably used when the peptide is relatively short (i.e., 10 kDa) and/or when it cannot be produced by recombinant techniques (i.e., not encoded by a nucleic acid sequence, such as a "Tag" further described hereinbelow) and therefore involve different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Briefly, an expression construct (i.e., expression vector), which includes an isolated polynucleotide (i.e., isolated from a naturally occurring source thereof, e.g., SEQ ID NO: 10) which comprises a nucleic acid sequence encoding the CCR2 amino acid sequence (optionally in frame fused to a nucleic acid sequence encoding the heterologous amino acid sequence) of the present invention positioned under the transcriptional control of a regulatory element, such as a promoter, is introduced into host cells.

For example, a nucleic acid sequence encoding a CCR2 peptide of the present invention (e.g., SEQ ID NO: 1) is ligated in frame to an immunoglobulin cDNA sequence (e.g., SEQ ID NOs: 3 and 5). It will be appreciated that, ligation of genomic immunoglobulin fragments can also be used. In this case, fusion requires the presence of immunoglobulin regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The nucleic acid sequences encoding the CCR2 amino acid sequence and immunoglobulin can be ligated in tandem into an expression construct (vector) that directs efficient expression in the selected host cells, further described hereinbelow. For expression in mammalian cells, pRK5-based vectors [Schall et al., Cell, 61:361-370 (1990)]; and CDM8-based vectors [Seed, Nature, 329: 840 (1989)] can be used. The exact junction can be created by removing the extra sequences between the designed junction codons using oligonucleotide-directed deletional mutagenesis [Zoller et al, Nucleic Acids Res., 10:6487 (1982); Capon et al., Nature, 337:525-531 (1989)]. Synthetic oligonucleotides can be used, in which each half is complementary to the sequence on either side of the desired junction; ideally, these are 11 to 48-mers. Alternatively, PCR techniques can be used to join the two parts of the molecule in-frame with an appropriate vector.

Methods of introducing the expression construct into a host cell are well known in the art and include, electroporation, lipofection and chemical transformation (e.g., calcium phosphate). See also Example 2 of the Examples section which follows.

The "transformed" cells are cultured under suitable conditions, which allow the expression of the chimeric molecule encoded by the nucleic acid sequence.

Following a predetermined time period, the expressed chimeric molecule is recovered from the cell or cell culture, and purification is effected according to the end use of the recombinant polypeptide.

Depending on the host/vector system utilized, any of a number of suitable transcription and translation elements including constitutive and inducible promoters, transcription enhancer elements, transcription terminators, and the like, can be used in the expression vector [see, e.g., Bitter et al., (1987) Methods in Enzymol. 153:516-544].

Other than containing the necessary elements for the transcription and translation of the inserted coding sequence (encoding the chimera), the expression construct of the present invention can also include sequences engineered to optimize stability, production, purification, yield or toxicity of the expressed fusion protein.

A variety of prokaryotic or eukaryotic cells can be used as host-expression systems to express the fusion protein coding sequence. These include, but are not limited to, microorganisms, such as bacteria transformed with a recombinant bacteriophage DNA, plasmid DNA or cosmid DNA expression vector containing the chimera coding sequence; yeast transformed with recombinant yeast expression vectors containing the chimera coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the chimera coding sequence. Mammalian expression systems are preferably used to express the chimera of the present invention.

The choice of host cell line for the expression of the molecules depends mainly on the expression vector. Eukaroyotic exoression systems are preferred (e.g., mammalian and insects) since they allow post translational modifications (e.g., glyccosylation). Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient expression. CDM8-based vectors can be used to transfect COS cells by the DEAE-dextran method (Aruffo et al., Cell, 61:1303-1313 (1990); Zettmeissl et al., DNA Cell Biol. US, 9:347-353 (1990)]. If larger amounts of protein are desired, the molecules can be expressed after stable transfection of a host cell line (see Example 2 of the Examples section). It will be appreciated that the presence of a hydrophobic leader sequence at the N-terminus of the molecule will ensure processing and secretion of the molecule by the transfected cells.

It will be appreciated that the use of bacterial or yeast host systems may be preferable to reduce cost of production. However since bacterial host systems are devoid of protein glycosylation mechanisms, a post production glycosylation may be needed.

In any case, transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant chimera molecule of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Molecules of the present invention are preferably retrieved in "substantially pure" form. As used herein, "substantially pure" refers to a purity that allows for the effective use of the protein in the diverse applications, described hereinbelow.

Chimeric molecules comprising immunoglobulin amino acid sequence can be conveniently purified by affinity chromatography. The suitability of protein A as an affinity ligand depends on the species and isotype of the immunoglobulin Fc domain that is used in the chimera. Protein A can be used to purify chimeric molecules that are based on human γ1, γ2, or γ4 heavy chains [Lindmark et al., J. Immunol. Meth., 62:1-13 (1983)]. Protein G is preferably used for all mouse isotypes and for human γ3 [Guss et al., EMBO J., 5:1567-1575 (1986)]. The solid support to which the affinity ligand is attached is most often agarose, but other solid supports are also available. Mechanically stable solid supports such as controlled pore glass or poly(styrenedivinyl)benzene allow for faster flow rates and shorter processing times than can be achieved with agarose. The conditions for binding the chimeric molecules to the protein A or G affinity column are dictated entirely by the characteristics of the Fc domain; that is, its species and isotype. Generally, when the proper ligand is chosen, efficient binding occurs directly from unconditioned culture fluid. One distinguishing feature of chimeric molecules of this aspect of the present invention is that, for human .gamma.1 molecules, the binding capacity for protein A is somewhat diminished relative to an antibody of the same Fc type. Bound chimeric molecules of this aspect of the present invention can be efficiently eluted either at acidic pH (at or above 3.0), or in a neutral pH buffer containing a mildly chaotropic salt. This affinity chromatography step can result in an chimeric molecule preparation that is >95% pure. Medical grade purity is essential for therapeutic applications.

Other methods known in the art can be used in place of, or in addition to, affinity chromatography on protein A or G to purify chimeric molecules which include an immunoglobulin portion. Such chimeric molecules behave similarly to antibodies in thiophilic gel chromatography [Hutchens et al., Anal. Biochem., 159:217-226 (1986)] and immobilized metal chelate chromatography [Al-Mashikhi et al., J. Dairy Sci., 71:1756-1763 (1988)]. In contrast to antibodies, however, their behavior on ion exchange columns is dictated not only by their isoelectric points, but also by a charge dipole that may exist in the molecules due to their chimeric nature.

It will be appreciated that the molecules of the present invention may be used to bind any ligand which binds CCR2 such as through the E3 domain thereof. These may include CCL7, CCL8 and CCL13 [D'Ambrosio (2003) J. Immunol. Methods 273:3-13].

Molecules of this aspect of the present invention may be used to treat MCP-1/CCR2 associated diseases.

Thus, according to another aspect of the present invention, there is provided a method of treating MCP-1/CCR2 associated disease in a subject in need thereof. The method comprising administering to the subject a therapeutically effective amount of the molecules of the present invention, thereby treating the MCP-1/CCR2 associated disease in the subject.

As used herein the term "subject" refers to a mammal, preferably a human subject.

As used herein the term "treating" refers to preventing, curing, reversing, attenuating, alleviating, minimizing, suppressing or halting the deleterious effects of an MCP-1/CCR2 associated disease.

As used herein the phrase "MCP-1/CCR2 associated disease" refers to a disease which depends on the interaction between MCP-1 and its receptor, CCR2, for onset or progression.

Examples of MCP-1/CCR2 associated diseases include, but are not limited to, inflammatory diseases, necrosis, atherosclerosis, cancer (e.g., prostate cancer, mammary carcinoma, breast cancer, glioblastoma, esophagus cancer, neuroblastoma), multiple sclerosis, atheroma, monocytic leukemia, kidney diseases (e.g., glomerularnephritis), hamman-rich syndrome, endometriosis, rheumatoid arthritis, bronchiolitis, asthma, systemic lupus erythematosus, inflammatory bowel diseases (e.g., colitis), alveolitis, restinosis, brain trauma, psoriasis, idiopathic pulmonary fibrosis and transplant arteriosclerosis.

The molecule of the present invention can be administered to the subject per se, or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism. Preferably, the pharmaceutical composition is not immunogenic.

As used herein, the term "active ingredient" refers to the molecule of the present invention accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Thus for example, the pharmaceutically acceptable carrier of the present invention may comprise a lipoamine acid.

Alternatively, the pharmaceutically acceptable carrier used by the present invention may comprise an embedding material such as a polyol (i.e., a carbohydrate). Non-limiting examples of carbohydrates which are suitable for use as excipients include maltodextrin (e.g., Glucidex Roquette), trehalose (e.g., Trehalose Merck), cellobiose, glucose, fructose, maltulose, iso-maltulose, lactulose, maltose, gentobiose, lactose, isomaltose, maltitol (e.g., Maltisorb Roquette), lactitol, erythritol, palatinitol, xylitol, mannitol, sorbitol, dulcitol and ribitol, sucrose, raffinose, gentianose, planteose, verbascose, stachyose, melezitose, dextran and inositol.

Yet alternatively, the pharmaceutically acceptable carrier used by the present is a microsphere suitable for oral administration. For example, the microsphere can include a water insoluble matrix of organic material that is resistant to dissolution or acidic degradation at pH levels found in the stomach (e.g., a pH level lower than 4) essentially as described in U.S. Pat. No. 6,849,271 to Vaghefi, et al., which is fully incorporated herein by reference. Such organic matrix material can be, for example, triglyceride, hydrogenated vegetable oil, a wax or a mixture of waxes, polyalkoxyalkylether, polyalkoxyalkylester and water insoluble partially degraded proteins.

It will be appreciated that the bioconjugated polymer (e.g., the PEGylated CCR2 peptide of the present invention) can be used in, and as a part of, the pharmaceutically acceptable carrier, and thus serves as a carrier molecule for delivery of the CCR2 amino acid sequence, while at the same time serving as a component of the delivery vehicle. A preferred embodiment of this dual use is a liposomal vehicle, e.g., PEG-conjugated liposomes, as described e.g., in U.S. Pat. Appl. No. 20030186869 to Poiani, George et al., which is fully incorporated herein by reference.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

It will be appreciated that the molecule (e.g., chimeric proteinicious) of this aspect of the present invention can be provided to the subject by means of gene therapy. Hence the above-described mammalian expression construct can be administered to the subject employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the subject (i.e., ex-vivo gene therapy).

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence such as the Igκ leader sequence (e.g., SEQ ID NOs. 7 and 8). Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

The affinity of the CCR2 peptide of the present invention to MCP-1 allows use thereof in purification and detection of MCP-1.

Thus, according to yet another aspect of the present invention there is provided a molecule comprising a tag and the CCR2 peptide of the present invention.

As used herein the term "tag" refers to a moiety which is specifically recognized by a binding partner such as an antibody, a chelator or an avidin (biotin) molecule. The tag can be placed C-terminally or N-terminally of the CCR2 peptide, as long as it does not interfere with a biological activity thereof (e.g., MCP-1 binding).

For example, a tag polypeptide has enough residues to provide an epitope (i.e., epitope tag) against which an antibody thereagainst can be made, yet is short enough such that it does not interfere with biological activity of the CCR2 peptide. The epitope tag preferably also is fairly unique so that the antibody thereagainst does not substantially cross-react with other epitopes. Suitable tag polypeptides generally have at least six amino acid residues and usually between about 8-50 amino acid residues (preferably between about 9-30 residues). Preferred are poly-histidine sequences, which bind nickel, allowing isolation of the tagged protein by Ni-NTA chromatography as described (Lindsay et al. Neuron 17:571-574 (1996)], for example.

Such epitope-tagged forms of the CCR2 are desirable, as the presence thereof can be detected using a labeled antibody against the tag polypeptide. Also, provision of the epitope tag enables the CCR2 peptide of the present invention to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-3616 (1985)]; and the Herpes Simplex virus glycoprotein D (gD) tag and its antibody. Paborsky et al., Protein Engineering, 3(6):547-553 (1990). Other tag polypeptides have been disclosed. Examples include the Flag-peptide [Hopp et al., BioTechnology, 6:1204-1210 (1988)]; the KT3 epitope peptide [Martin et al., Science, 255:192-194 (1992)]; an α-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)]. Once the tag polypeptide has been selected, an antibody thereto can be generated using methods which are well known in the art. Such antibodies are commercially available such as from Sigma, St. Louis. USA.

The molecules of this aspect of the present invention can be used to isolate MCP-1 from biological samples or detect presence of MCP-1 therein.

As used herein the phrase "biological sample" refers to a biological fluid such as blood, serum, plasma, lymph, bile fluid, urine, saliva, sputum, synovial fluid, semen, tears, cerebrospinal fluid, bronchioalveolar large fluid, ascites fluid, pus, conditioned medium and the like in which MCP-1 is present.

Isolation of MCP-1 according to this aspect of the present invention is effected by contacting the biological sample with the molecule of this aspect of the present invention, such that MCP-1 and the molecule form a complex (using buffer, temperature conditions which allow binding of the molecule to MCP-1, see for Example Datta-Mannan and Stone 2004, supra); and isolating the complex to thereby isolate MCP-1 from the biological sample.

In order to isolate the complex, the molecule is preferably immobilized on a solid support. As used herein the phrase "solid support" refers to a non-aqueous matrix to which a reagent of interest (e.g., the molecule of this aspect of the present invention) can adhere. Examples of solid supports, include, but are not limited to, solid supports formed partially or entirely of glass (e.g., controlled pore glass), polysaccharides (e.g., agarose), polyacrylamides, polystyrene, polyvinyl alcohol and silicones. In certain embodiments, depending on the context, the solid support can comprise the well of an assay plate; in others it is a purification column (e.g., an affinity chromatography column). This term also includes a discontinuous solid phase of discrete particles, such as those described in U.S. Pat. No. 4,275,149.

Alternatively, such molecules can be used to detect the levels of MCP-1 in biological samples. For diagnostic applications, molecules typically will be labeled with a detectable moiety. The detectable moiety can be any one which is capable of producing, either directly or indirectly, a detectable signal. For example, the detectable moiety may be a radioisotope, a fluorescent or chemiluminescent compound, or a tag (such as described hereinabove and to which a labeld antibody can bind). The molecules of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc., 1987).

The molecules of this aspect of the present invention can be included in a diagnostic kit, in which the molecule and optionally solid support and imaging reagents (e.g., antibodies, chromogenic substrate etc.) can be packaged in suitable containers with appropriate buffers and preservatives and used for diagnosis.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Prostate Cancer Patients Display a Specific Selective Antibody Response to MCP-1

The connection between CCL2 and prostate cancer was established using an ELISA test for the presence of autoantibodies to various chemokines, including MCP-1 (CCL2), in prostate cancer patients.

Materials and Experimental Procedures

Patient specimens—The human experimental work was conducted in collaboration with the Departments of Urology of CARMEL and RAMBAM medical centers in Haifa, Israel. All sera and tissue samples were obtained from patients of RAMBAM hospital under Helsinki Committee Approval No. 1822 dated Nov. 11, 2003. Pathological analysis was conducted by Prof. Avi Stein from the Department of Urology, CARMEL medical center. Clinical data of the patients is summarized in Table 1, below.

Determination of antibody (Ab) titers—Ab titer against each tested chemokine was detected using an ELISA test as previously described in details (Wildbaum, G., M. Nahir, and N. Karin. 2003. Beneficial autoimmunity to proinflammatory mediators restrains the consequences of self-destructive immunity. Immunity 19:679). Recombinant human chemokines: SDF-1 (CXCL12), MIP-1α (CCL3), MIP-1β (CCL4), IL-8 (CXCL8), IP-10 (CXCL10), MIP-3α (CCL20), MIP-3β (CCL-19), Lymphotactin (XCL1), MIG (CXCL9), RANTES (CCL5), MCP-3 (CCL7) and MCP-1 (CCL2) were all purchased from PeproTech, Rocky Hill, N.J. Human MIF was purchased from R&D Systems (Minneapolis, N. Mex.).

Results

Prostate Cancer Patients Display a Significant Autoantibody Titer to MCP-1

Sera from 23 prostate cancer patients, 21 individuals with benign prostate hypertrophy (BPH), and 11 control subjects (Table 3, below) were tested for the presence of autoantibodies to various chemokines, particularly those that have been implicated with cancer, including SDF-1 (CXCL12), MIF, MIP-1α (CCL3), MIP-1β (CCL4), IL-8 (CXCL8), IP-10 (CXCL10), MIP-3α (MCP-10), MIP-3β (CCL-19), Lymphotactin (XCL1), MIG (CXCL9), RANTES (CCL5), MCP-3 (CCL7) and MCP-1 (MCP-1).

TABLE 3

| Patient Demographics and Characteristics | |
|---|---|
| Number of prostate cancer patients enrolled | 2 |
| Age, years [median (range)] | 74 (64-81) |
| Prostate-specific antigen (PSA), ng/ml [median (range)] | 382 (3.7-3400) |
| Primary therapy | |
| Hormone therapy | 1[a] |
| Radical prostatectomy | 1 |
| TURP | 3 |
| Radiation | 2 |
| Gleason score | |
| ≦6 | 3 |
| 7 | 18 |
| ≧8 | 2 |
| Number of Benign Prostatic Hyperplasia patients enrolled | 21 |
| Age, years [median (range)] | 71 (64-79) |
| Prostate-specific antigen (PSA), ng/ml [median (range)] | 6.8 (4.3-8.9) |
| Number of healthy controls enrolled | 10 |
| Age, years [median (range)] | 70 (62-75) |

[a]Values denote the number of patients in each group

Of all tested chemokines, prostate cancer patients mounted a highly significant antibody titer exclusively to MCP-1 (FIG. 1a, $\log_2$ Ab titer of 11.85±0.8). The baseline titer of anti MCP-1 antibodies ($\log_2$) in healthy individuals and BPH patients was 5-6, and did not differ from the one observed in response to any of the other chemokines. Thus, prostate cancer patients display a highly specific and selective antibody response to MCP-1 (FIG. 1a, p<0.01). Statistical analysis revealed that about 82% of prostate cancer patients (19/23), and only 4.7% (1/21) of patients with non-malignant BPH, displayed a significant response (log 2Ab titer>10, p<0.01) to MCP-1 (FIG. 1b).

These results suggested that inhibition of MCP-1 CCR2 interaction may be used to suppress cancer and other diseases which are regulated by MCP-1/CCR2.

Example 2

Figure 2:
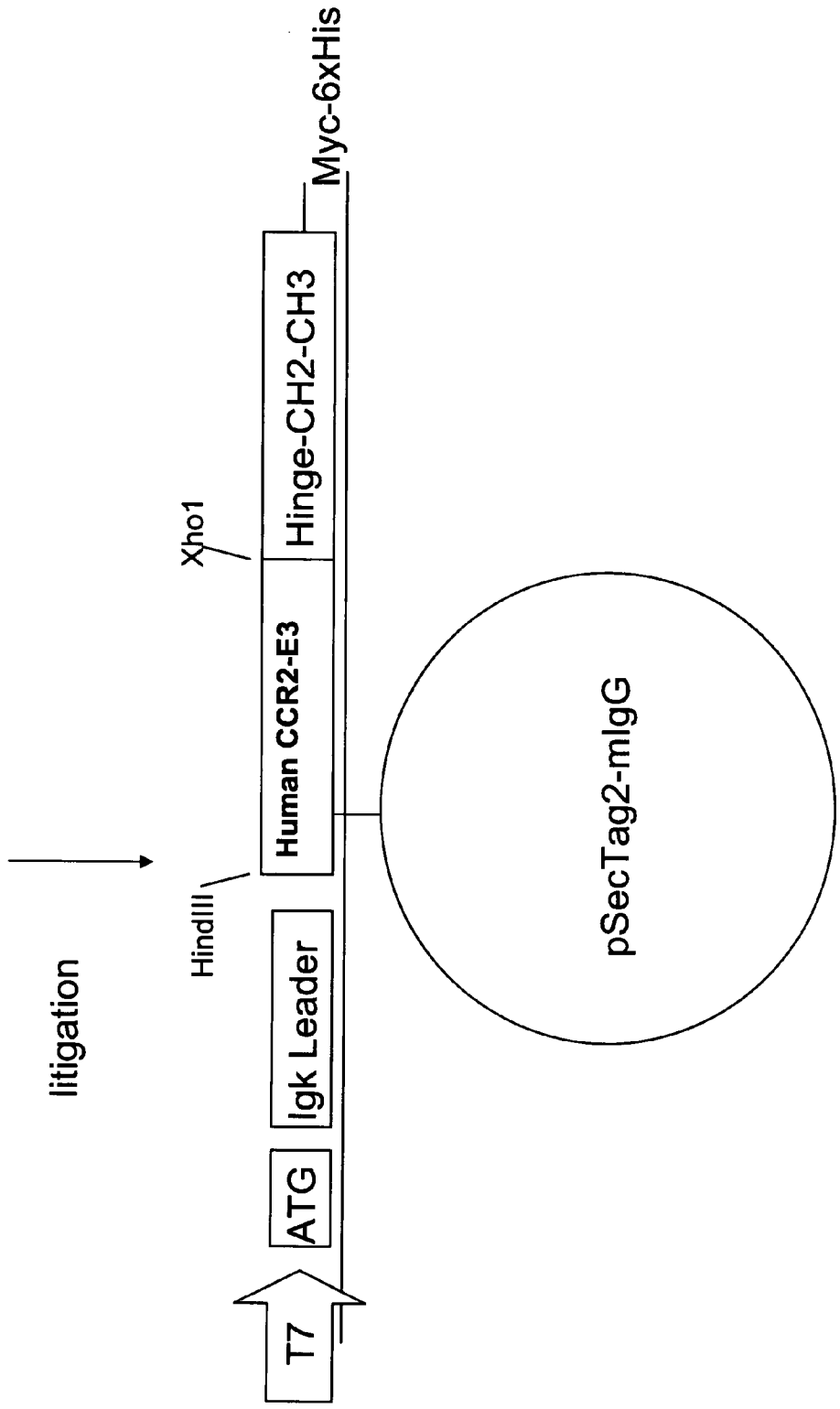
FIG. 2 is a schematic illustration depicting the generation of the expression construct encoding the human Ig-CCR2 peptide of the present invention (Ig-E3, as set forth in SEQ ID NO: 1).

Generation of CCR2 Chimeric Peptide (E3-Ig) and Stable Expression in Cell Lines Materials and Experimental Procedures
Generation of CCR2(E3)-IgG Construct
FIG. 2 shows an illustration of the CCR2(E3)-IgG chimera expressing construct. The IgG1 construct was produced according the basic protocol that was previously utilized for the generation of CTLA4-Ig (Van Oosterhout, A. J., C. L. Hofstra, R. Shields, B. Chan, I. Van Ark, P. M. Jardieu, and F. P. Nijkamp. 1997. Murine CTLA4-IgG treatment inhibits airway eosinophilia and hyperresponsiveness and attenuates IgE upregulation in a murine model of allergic asthma. Am J Respir Cell Mol Biol 17:386) with modifications: cDNA encoding the constant region (Hinge-CH2-CH3) of human IgG1 heavy chain has been cloned from LPS and IL-4 activated peripheral blood mononuclear cells (PBMC) onto pSecTag2/Hygro B (Invitrogen, San Diego, Calif.). Human CCR2-E3 was subcloned from LPS activated human PBMC using primers encoding part of the 6 domain of CCR2 (E3, SEQ ID NOs: 1 and 2, respectively) as follows: sense: cccaagcttggcctgagtaactgtgaaag (SEQ ID NO: 12), antisense: ccgctcgagagtctctgtcacctgcgtgg (SEQ ID NO: 13). Following sequence verification the amplified PCR product was cloned into a pSec-Tag2 vector (Invitrogen, San Diego, Calif.). Hinge-CH2-CH3 of the human IgG Fcγ was ligated to the plasmid (pSec-CCR2) down stream of the CCR2 (E3) to create a fusion protein CCR2-IgG.

Generation of Stable pSec-CCR2(E3)-IgG-Expressing Cell Lines
The pSec-CCR2(E3)-IgG plasmid was co-transfected into the DG44 CHO cells (DHFR$^{-/-}$) (provided by Dr. Lawrence Chasin from Columbia university, USA), with CHO DHFR minigene vector using jet PEI (Polypluse transfection—Illkirch Cedex, France) according the manufacturer's protocol. Stable transfectent cells were selected in medium containing hygromycine (200 μg/ml). The CCR2(E3)-IgG fusion protein was purified from the supernatants by a protein G-Sepharose column obtained from Amersham Biosciences (Uppsia, Sweden) and verified by western blot analysis using the goat anti human IgG-HRP (Sigma, St. Louis, Mo.).

Example 3

CCR2(E3)-IgG Binds Specifically to MCP-1

The ability of the E3 domain of CCR2 to bind MCP-1 was addressed by an ELISA assay.
Materials and Experimental Procedures
ELISA—The binding specificity of CCR2(E3)-IgG to various commercially available human chemokines (Pepro- Tech, Rocky Hill, N.J.) was determined by direct ELISA as follows: 96-well ELISA plates (Nunc, Roskilde, Denemark) were coated with 100 ng/ml of each chemokine, washed and blocked with 1% BSA/PBS. CCR2(E3)-IgG at a concentration 5 μg/ml was then added. HRP labeled mouse anti human Ig (Jackson, Pa.) was added as a second Antibody. Results are shown as O.D. reading at 450 nm. Anti CCL2 monoclonal antibody (MAB679; R&D Systems, Minneapolis, N. Mex.) was used as a positive control (1 μg/ml).

Results
Binding of CCR2(E3)-IgG to various cytokines was determined by an ELISA. As shown in FIG. 3, the E3 domain of CCR2 was sufficient to bind MCP-1, exhibiting almost four times higher binding to this chemokine as compared to other factors tested.

Example 4

CCR2(E3)-IgG Inhibits MCP-1-Induced Cell Migration

Materials and Experimental Procedures
Cell Lines
THP-1 cells were obtained from American Type Culture Collection (ATCC, Rockville, Md. with ATCC Accession No. TIB-202) and grown according to the manufacturers protocol.

Cell migration assay—The ability of CCR2(E3)-IgG to inhibit MCP-1 induced migration of THP-1 cells was tested. Chemotaxis assays were conducted using a TransWell chamber (Corning Costar, Cambridge, Mass.). THP-1 cells with medium ($1 \times 10^6$ cells/well) were added to the upper chamber of the Transwell, after equilibration of the lower chambers with medium, recombinant human MCP-1 (R&D Systems, Minneapolis, N. Mex.), that were, or were not, supplemented with the soluble CCR2(E3)-IgG. Transwells were then incubated for 3 hours at 37° C. in humidified air containing 7.5% $CO_2$. Migrating monocytes were collected from the lower chamber and counted.

Results
FIG. 4 shows that the soluble CCR2(E3)-IgG significantly and pronouncedly (90%) blocked MCP-1 induced migration of THP-1 cells in a dose dependent manner.

Example 4

CCR2(E3)-IgG Radically Demotes PC-3 Tumor Growth, and Reduces VEGF Expression Materials and Experimental Procedures
Treatment of mice with CCR2(E3)-IgG—Three groups of six SCID/Bg mice were subcutaneously administered with $5 \times 10^6$ PC-3 Luc cells/mouse (El Hilali et al. Clin Cancer Res. 2005 Feb. 1; 11(3):1253-8.)

The first group was subjected to repeated administrations of CCR2(E3)-IgG (200 ug/mouse, i.v., at four day intervals). The second group was administered with a matching amount of PBS, and the third with isotype matched control IgG. For late therapy (i.e., treatment of an established tumor), administration was started 18 days after administration with PC-3 cells.

Detection of VEGF—See de Wet, J. R., K. V. Wood, M. DeLuca, D. R. Helinski, and S. Subramani. 1987. Firefly luciferase gene: structure and expression in mammalian cells.

*Mol Cell Biol* 7: 725; Rubio, N., M. M. Villacampa, and J. Blanco. 1998. Traffic to lymph nodes of PC-3 prostate tumor cells in nude mice visualized using the luciferase gene as a tumor cell marker. *Lab Invest* 78:1315; Rubio, N., M. Lorgans measured using prostate tumor PC-3 cells expressing the luciferase gene as a quantifiable tumor cell marker. *Prostate* 44:133; Harlow, E., and D. Lane. 1988. *Antibodies, a laboratory manual*. Cold Spring Harbor Laboratory, New York. Animals were sacrificed on day 30 and tumors were retrieved and sectioned. VEGF was detected using rabbit anti VEGF from Santa Cruz. (If you need the cat number I can provide you tomorrow).

Luciferase activity—As previously described see El Hilali Clin Cancer Res. 2005 Feb. 1; 11(3):1253-8. Briefly, Animals were sacrificed on day 30 using $CO_2$. Lungs and bone were retrieved and frozen in liquid nitrogen. The frozen tissue was then ground into powder and lysis buffer was added (Promega). Samples were vortexed for a few seconds and the mixture was centrifuged for 20 minutes (13000 rpm). Luciferase substrate was then added.

Results

Figure 5A:
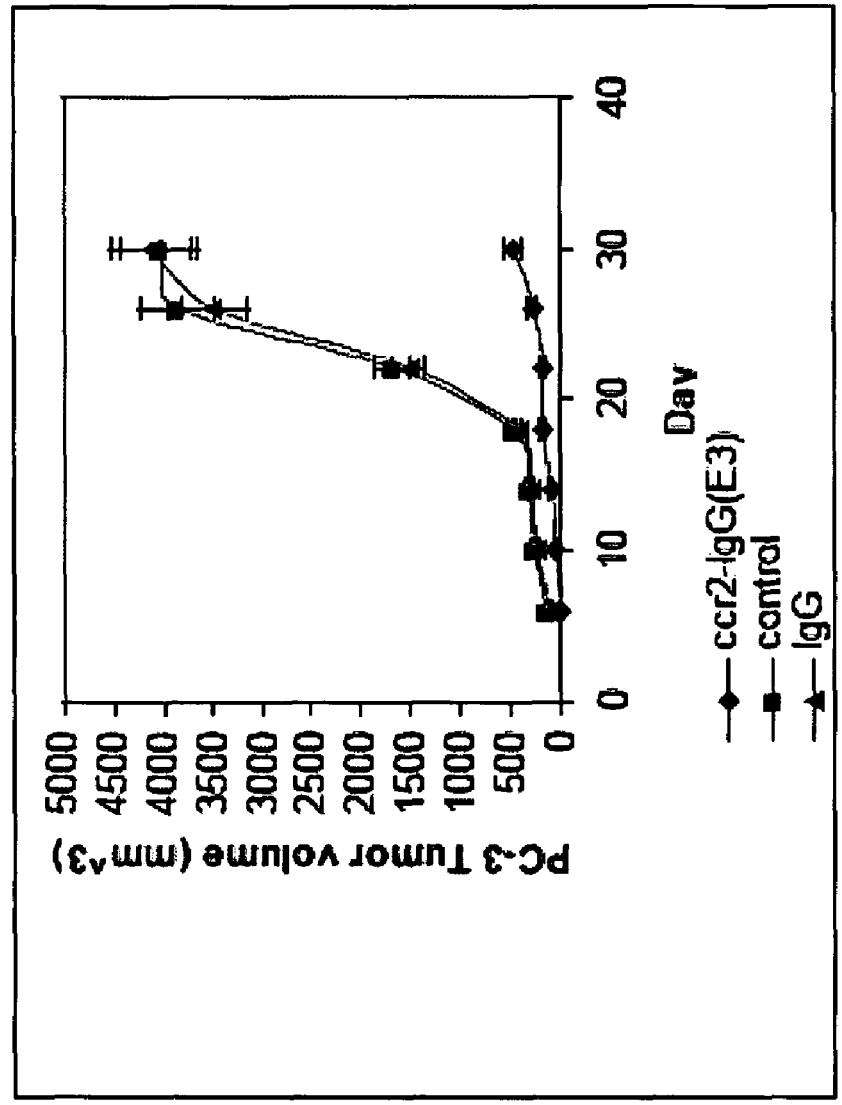

Treatment with CCR2(E3)-Ig radically demotes PC-3 tumor growth—as shown in FIG. 5a, repeated administration of CCR2(E3)-IgG completely inhibited the PC-3 tumor growth, as compared to tumors developed in mice administered with PBS or with control IgG.

Late therapy (day 18) with CCR2-Ig blocks the development of the pre-established primary tumor and its ability to form metastases—FIG. 5b clearly shows that even when CCR2(E3)-IgG was administered following tumor development (day 18 of cell injection), the blockage of CCL2 dramatically reduced the development of the primary tumor and its ability to form metastases. Even after intermediate time following tumor cell administration (8 days) CCR2(E3)-IgG was able to inhibit tumor development.

Figure 5C:
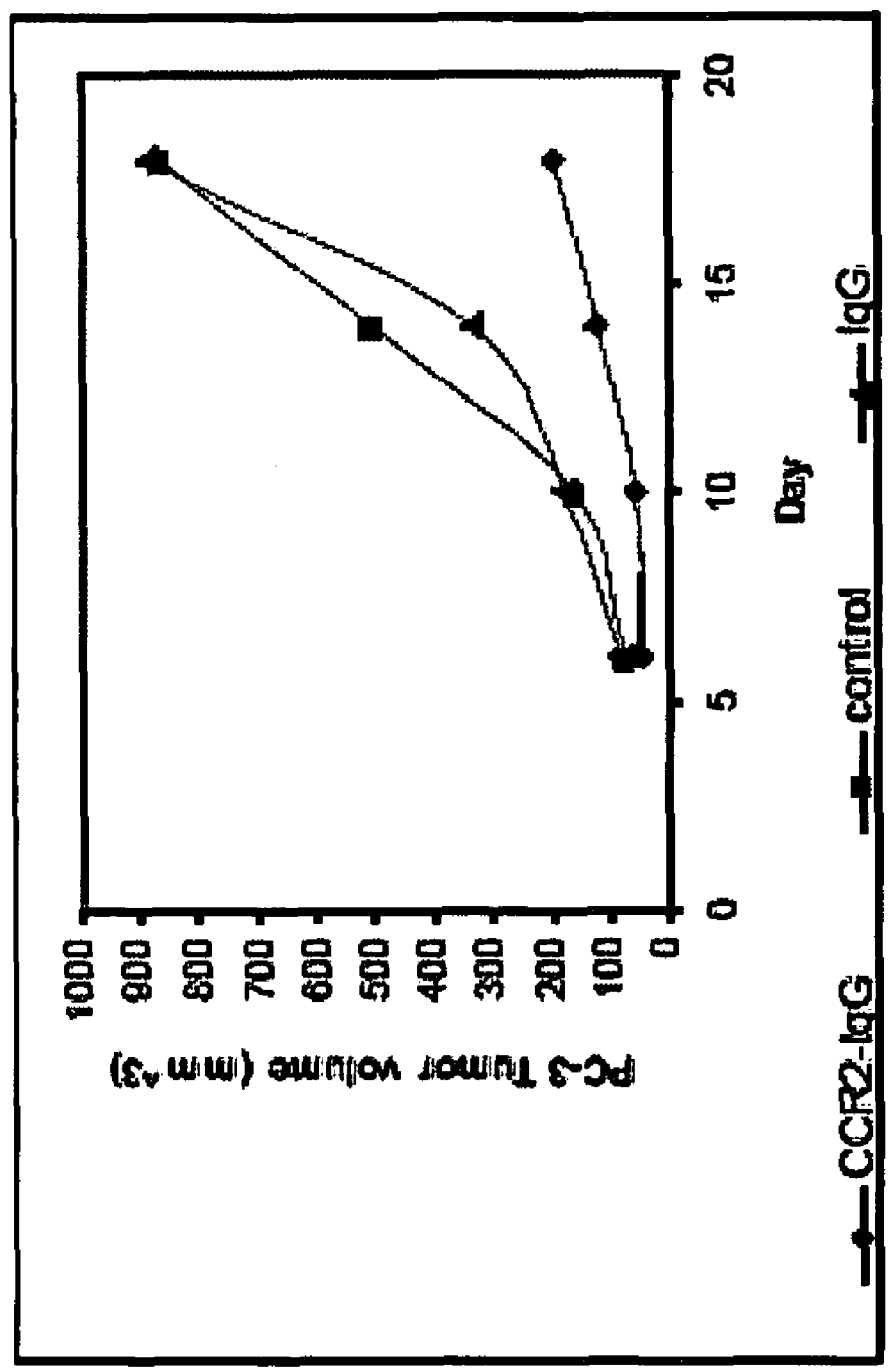

Treatment with CCR2(E3)-Ig reduces tumor metastasis—As shown in FIG. 5c, treatment of mice with CCR2(E3)-IgG significantly inhibited tumor metastasis to lung and bone tissue as indicated by the reduction of luciferase activity. Luciferase activity in both tissues was reduced by 4-10 folds as compared to untreated animals and overall reached the same minimal level (i.e., about 0.5).

Treatment with CCR2(E3)-IgG radically reduces VEGF expression—As shown in FIGS. 6a-f, administration of CCR2(E3)-IgG (FIGS. 6a, d) dramatically reduced the VEGF expression at the tumor site as compared to isotype matched control IgG (FIGS. 6b, e) and PBS (FIGS. 6c, f). This suggests that blockade of CCR2 pathway inhibits the tumor-inducing activity of VEGF.

Example 5

CCL2 Induced Migration of PC-3 Cells is Inhibited by CCR2(E3)-IgG

Materials and Experimental Procedures

Cell migration assay—cell migration was determined using the CytoSelect kit of Cell Biolabs, San Diego, Calif. Anti CCL2 was obtained from Dr. Martinez and Dr. Melado—Department of Immunology and Oncology, Centro Nacional de Biotecnologia, UAM Campus de Cantoblanco, Madrid, Spain. Briefly, PC-3 cells ($10^6$/well) were added to the upper chamber of the transwell plate and CCL2 (recombinant human MCP-1, RHMCP-1; 20 ng/ml) was added to the lower well, that was also supplemented with anti CCL2 (50 µg) and/or CCR2(E3)-IgG (200 µg) as shown in the FIG. 7. Following 2 hours of incubation at 37° C. migrating PC-3 cells were counted by a FACS. Result are shown as mean of triplicates±SE.

Results

Figure 7:
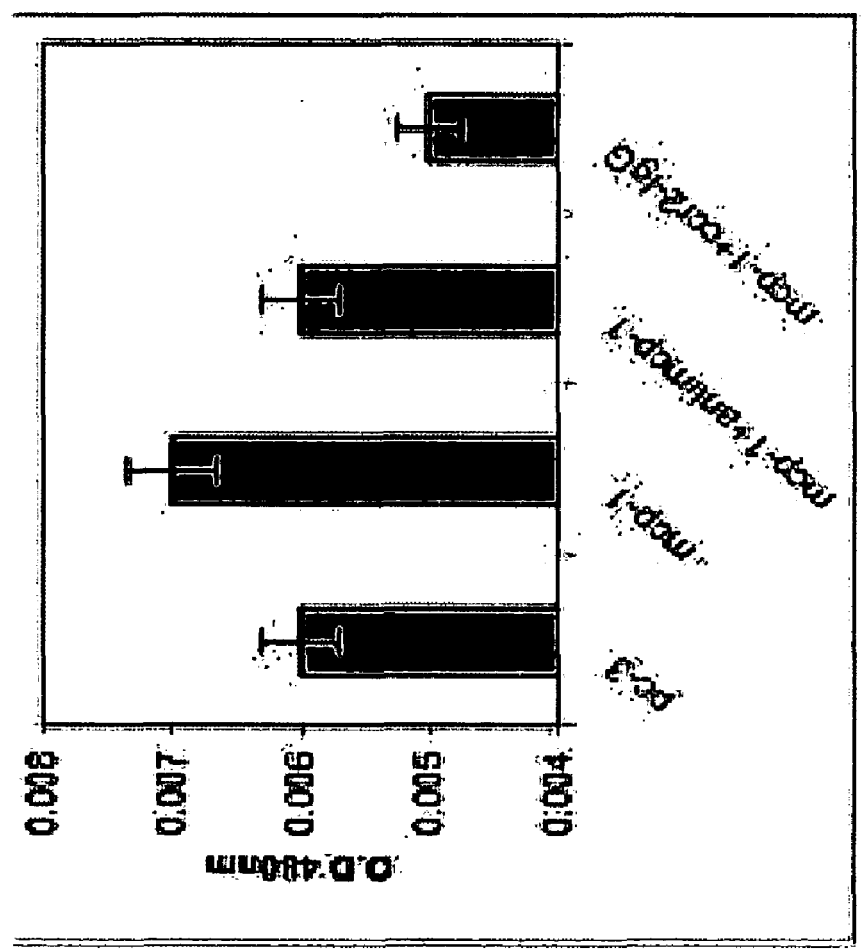
FIG. 7 is a bar graph depicting cell migration of CCL2 treated PC3 cells, as determined by optical density. PC3 cells were treated with either CCL2 (MCP-1), CCL2 together with an antibody against CCL2 (MCP-1+anti MCP-1), CCL2 together with CCR2(E3)-IgG (MCP-1+CCR2(E3)-IgG) and control cells which were not ligand-treated.

Among the potential mechanism of action of CCL2 on prostate cancer cells is that it attracts tumor cells. As can be seen in FIG. 7, CCL2 with CCR2-Ig better inhibits the migration of PC3 cells than anti CCL2 mAb.

Example 6

PEGylation of a CCR2 Amino Acid Sequence

To stabilize the CCR2 amino acid sequence of the present invention and in order to make it suitable for oral and/or paraenteral administration, a peptide having the following sequence: Lys Gly Leu Ser Asn Cys Glu Ser Thr Ser Gln Leu Asp Gln Ala Thr Gln Val Thr Glu Thr (SEQ ID NO: 11), which is identical to SEQ ID NO:1 except that a Lysine residue is added at its N-terminus, can be PEGylated using methods known in the art (e.g., Croyle, M. A., et al., 2000, Hum. Gene Ther. 11: 1721-1730; Croyle, M. A., et al., 2004, J. Virol. 78: 912-921). For example, monomethoxypoly(ethylene) glycol can be activated by succinimidyl succinate (which can be obtained from Sigma Chemicals, St. Louis, Mo.). Once activated, the polymer can be added to the CCR2 peptide in a weight ratio of about 10:1 (polymer:peptide) and the PEGylation reaction is further performed at 25° C. with gentle agitation. The reactions can be stopped by the addition of excess (e.g., of 10 fold) of lysine (Sigma Chemicals) with respect to the amount of PEG added. Unreacted PEG, excess lysine, and reaction by-products are eliminated by buffer exchange over a Micro-Bio Spin P-30 chromatography column (Bio-Rad) equilibrated with 100 mM potassium phosphate-buffered saline (pH 7.4).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A molecule comprising the amino acid sequence as set forth in SEQ ID NO: 14 or 15.

2. The molecule of claim 1, attached to a non-proteinaceous moiety.

3. The molecule of claim 2, wherein said non-proteinaceous moiety is selected from the group consisting of polyethylene glycol (PEG), Polyvinyl pyrrolidone (PVP), poly(styrene comaleic anhydride) (SMA), and divinyl ether and maleic anhydride copolymer (DIVEMA).

4. A pharmaceutical composition comprising the molecule of claim 1 and a pharmaceutically acceptable carrier.

* * * * *

SEQUENCE LISTING

<160> NUMBER OF SEQ ID NOS: 15

<210> SEQ ID NO 1
<211> LENGTH: 60
<212> TYPE: DNA
<213> ORGANISM: Artificial sequence
<220> FEATURE:
<223> OTHER INFORMATION: Homo sapiens CCR2 E3 domain coding sequence

<400> SEQUENCE: 1
ggcctgagta actgtgaaag caccagtcaa ctggaccaag ccacgcaggt gacagagact    60

<210> SEQ ID NO 2
<211> LENGTH: 20
<212> TYPE: PRT
<213> ORGANISM: Artificial sequence
<220> FEATURE:
<223> OTHER INFORMATION: Homo sapiens CCR2 E3 domain amino acid sequence

<400> SEQUENCE: 2

Gly Leu Ser Asn Cys Glu Ser Thr Ser Gln Leu Asp Gln Ala Thr Gln
1               5                   10                  15

Val Thr Glu Thr
            20

<210> SEQ ID NO 3
<211> LENGTH: 681
<212> TYPE: DNA
<213> ORGANISM: Mus musculus

<400> SEQUENCE: 3
gtgcccaggg attgtggttg taagccttgc atatgtacag tcccagaagt atcatctgtc    60
ttcatcttcc ccccaaagcc caaggatgtg ctcaccatta ctctgactcc taaggtcacg   120
tgtgttgtgg tagacatcag caaggatgat cccgaggtcc agttcagctg gtttgtagat   180
gatgtggagg tgcacacagc tcagacgcaa ccccgggagg agcagttcaa cagcactttc   240
cgctcagtca gtgaacttcc catcatgcac caggactgcc tcaatggcaa ggagttcaaa   300
tgcagggtca acagtgcagc tttccctgcc cccatcgaga aaaccatctc caaaaccaaa   360
ggcagaccga aggctccaca ggtgtacacc attccacctc caaggagca gatggccaag   420 gataaagtca gtctgacctg catgataaca gacttcttcc ctgaagacat tactgtggag   480
tggcagtgga atgggcagcc agcggagaac tacaagaaca ctcagcccat catggacaca   540
gatggctctt acttcgtcta cagcaagctc aatgtgcaga gagcaactg ggaggcagga   600 aatactttca cctgctctgt gttacatgag ggcctgcaca accaccatac tgagaagagc   660
ctctcccact ctcctggtaa a                                              681

<210> SEQ ID NO 4
<211> LENGTH: 227
<212> TYPE: PRT
<213> ORGANISM: Mus musculus

<400> SEQUENCE: 4

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
                20                  25                  30

Ile Thr Leu Thr Pro Lys Val Thr Cys Val Val Val Asp Ile Ser Lys
            35                  40                  45

```
Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
 65                  70                  75                  80

Arg Ser Val Ser Glu Leu Pro Ile Met His Gln Asp Cys Leu Asn Gly
                 85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Lys
225

<210> SEQ ID NO 5
<211> LENGTH: 705
<212> TYPE: DNA
<213> ORGANISM: Homo sapiens
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t

<400> SEQUENCE: 5
ctcgagccca aatcttgtga caaaactcac acatgcccac cgtgcccagc acctgaactc      60
ctggggggac cgtcagtctt cctcttcccc ccaaaaccca aggacaccct catgatctcc     120
cggacccctg aggtcacatg cgtggtggtg gacgtgagcc acgaagaccc tgaggtcaag     180
ttcgactggt acgtggacgg cgtggaggtg cataatgcca agacaaagcc gcggaggag     240 cagtacaaca gcacgtaccg tgtggtcagc gtcctcaccg tcctgcacca ggactggctg     300
aatggcaagg agtacaagtg caaggtctcc aacaaagccc tcccagcccc caccgagaaa     360
accatctcca aagccaaagg gcagccccga gaaccacagg tgtacaccct gcccccatcc     420
cgggaggaga tgaccaagaa ccaggtcagc ctgacctgcc tggtcaaagg cttctatccc     480
agcgacatcg ccgtggagtg ggagagcaat gggcagccgg agaacaacta caagaccacg     540
cctcccgtgc tggactccga cggctccttc ttcctctata gcaagctcac cgtggacaag     600
agcaggtggc agcaggggaa cgtcttctca tgctccgtga tgcatgaggn cctgcacaac     660
cactacacgc agaagagcct ctccctgtnc ccgggtaaag ggccc                    705

<210> SEQ ID NO 6
<211> LENGTH: 234
```

```
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asp Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Thr Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Pro
225                 230

<210> SEQ ID NO 7
<211> LENGTH: 63
<212> TYPE: DNA
<213> ORGANISM: Artificial sequence
<220> FEATURE:
<223> OTHER INFORMATION: Ig kappa leader coding sequence

<400> SEQUENCE: 7
atggagacag acacactcct gctatgggta ctgctgctct gggttccagg ttccactggt      60
gac                                                                   63

<210> SEQ ID NO 8
<211> LENGTH: 21
<212> TYPE: PRT
<213> ORGANISM: Artificial sequence
<220> FEATURE:
<223> OTHER INFORMATION: Ig kappa leader amino acid sequence

<400> SEQUENCE: 8

Met Glu Thr Asp Thr Leu Leu Leu Trp Val Leu Leu Leu Trp Val Pro
1               5                   10                  15

Gly Ser Thr Gly Asp
            20
```

```
<210> SEQ ID NO 9
<211> LENGTH: 40
<212> TYPE: PRT
<213> ORGANISM: Artificial sequence
<220> FEATURE:
<223> OTHER INFORMATION: A polypeptide containing Two tandem CCR2 E3
      domain

<400> SEQUENCE: 9

Gly Leu Ser Asn Cys Glu Ser Thr Ser Gln Leu Asp Gln Ala Thr Gln
1               5                   10                  15

Val Thr Glu Thr Gly Leu Ser Asn Cys Glu Ser Thr Ser Gln Leu Asp
            20                  25                  30

Gln Ala Thr Gln Val Thr Glu Thr
        35                  40

<210> SEQ ID NO 10
<211> LENGTH: 120
<212> TYPE: DNA
<213> ORGANISM: Artificial sequence
<220> FEATURE:
<223> OTHER INFORMATION: A polynucleotide expressing two tandem CCR2 E3
      domain

<400> SEQUENCE: 10
ggcctgagta actgtgaaag caccagtcaa ctggaccaag ccacgcaggt gacagagact    60
ggcctgagta actgtgaaag caccagtcaa ctggaccaag ccacgcaggt gacagagact   120

<210> SEQ ID NO 11
<211> LENGTH: 21
<212> TYPE: PRT
<213> ORGANISM: Artificial sequence
<220> FEATURE:
<223> OTHER INFORMATION: A peptide containing CCR2 E3 domain added with
      a N' Lys residue for PEGylation

<400> SEQUENCE: 11

Lys Gly Leu Ser Asn Cys Glu Ser Thr Ser Gln Leu Asp Gln Ala Thr
1               5                   10                  15

Gln Val Thr Glu Thr
            20

<210> SEQ ID NO 12
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 12
cccaagcttg gcctgagtaa ctgtgaaag                                      29

<210> SEQ ID NO 13
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 13
ccgctcgaga gtctctgtca cctgcgtgg                                      29

<210> SEQ ID NO 14
<211> LENGTH: 311
<212> TYPE: PRT
```

-continued

<213> ORGANISM: Artificial sequence
<220> FEATURE:
<223> OTHER INFORMATION: A polypeptide composed of Ig kappa leader, CCR2
      E3 domain, Immunoglobulin Heavy chain constant region and a 6XHis
      tag

<400> SEQUENCE: 14

Met Glu Thr Asp Thr Leu Leu Leu Trp Val Leu Leu Trp Val Pro
1               5                   10                  15

Gly Ser Thr Gly Asp Ala Ala Gln Pro Ala Arg Arg Ala Arg Arg Thr
            20                  25                  30

Tyr Lys Leu Gly Leu Ser Asn Cys Glu Ser Thr Ser Gln Leu Asp Gln
            35                  40                  45

Ala Thr Gln Val Thr Glu Thr Leu Glu Pro Lys Ser Cys Asp Lys Thr
50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
            115                 120                 125

Lys Thr Lys Pro Arg Glu Glu Gln Tyr Asn Ser Thr Tyr Arg Val Val
            130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Glu Glu Met Thr Lys Asn Gln Val Ser Leu Thr Cys
            195                 200                 205

Leu Val Lys Gly Phe Tyr Pro Ser Asp Ile Ala Val Glu Trp Glu Ser
210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
            275                 280                 285

Gly Pro Glu Gln Lys Leu Ile Ser Glu Glu Asp Leu Asn Ser Ala Val
            290                 295                 300

Asp His His His His His
305                 310

<210> SEQ ID NO 15
<211> LENGTH: 305
<212> TYPE: PRT
<213> ORGANISM: Artificial sequence
<220> FEATURE:
<223> OTHER INFORMATION: A polypeptide composed of Ig kappa leader, CCR2
      E3 domain and an Immunoglobulin Heavy chain constant region

<400> SEQUENCE: 15

Met Glu Thr Asp Thr Leu Leu Leu Trp Val Leu Leu Trp Val Pro

-continued

```
1               5                   10                  15
Gly Ser Thr Gly Asp Ala Ala Gln Pro Ala Arg Arg Ala Arg Arg Thr
            20                  25                  30
Tyr Lys Leu Gly Leu Ser Asn Cys Glu Ser Thr Ser Gln Leu Asp Gln
            35                  40                  45
Ala Thr Gln Val Thr Glu Thr Leu Glu Pro Lys Ser Cys Asp Lys Thr
50                  55                  60
His Thr Cys Pro Pro Cys Pro Ala Pro Glu Leu Leu Gly Gly Pro Ser
65                  70                  75                  80
Val Phe Leu Phe Pro Pro Lys Pro Lys Asp Thr Leu Met Ile Ser Arg
            85                  90                  95
Thr Pro Glu Val Thr Cys Val Val Val Asp Val Ser His Glu Asp Pro
            100                 105                 110
Glu Val Lys Phe Asn Trp Tyr Val Asp Gly Val Glu Val His Asn Ala
            115                 120                 125
Lys Thr Lys Pro Arg Glu Glu Gln Tyr Asn Ser Thr Tyr Arg Val Val
            130                 135                 140
Ser Val Leu Thr Val Leu His Gln Asp Trp Leu Asn Gly Lys Glu Tyr
145                 150                 155                 160
Lys Cys Lys Val Ser Asn Lys Ala Leu Pro Ala Pro Ile Glu Lys Thr
            165                 170                 175
Ile Ser Lys Ala Lys Gly Gln Pro Arg Glu Pro Gln Val Tyr Thr Leu
            180                 185                 190
Pro Pro Ser Arg Glu Glu Met Thr Lys Asn Gln Val Ser Leu Thr Cys
            195                 200                 205
Leu Val Lys Gly Phe Tyr Pro Ser Asp Ile Ala Val Glu Trp Glu Ser
            210                 215                 220
Asn Gly Gln Pro Glu Asn Asn Tyr Lys Thr Thr Pro Pro Val Leu Asp
225                 230                 235                 240
Ser Asp Gly Ser Phe Phe Leu Tyr Ser Lys Leu Thr Val Asp Lys Ser
            245                 250                 255
Arg Trp Gln Gln Gly Asn Val Phe Ser Cys Ser Val Met His Glu Ala
            260                 265                 270
Leu His Asn His Tyr Thr Gln Lys Ser Leu Ser Leu Ser Pro Gly Lys
            275                 280                 285
Gly Pro Glu Gln Lys Leu Ile Ser Glu Glu Asp Leu Asn Ser Ala Val
            290                 295                 300
Asp
305
```